(12) United States Patent
Androphy et al.

(10) Patent No.: US 7,183,051 B2
(45) Date of Patent: Feb. 27, 2007

(54) DIAGNOSIS AND TREATMENT OF CANCER

(75) Inventors: Elliot J. Androphy, Natick, MA (US); Nishita Doshi, Cambridge, MA (US); Alexandra Belayew, Esneux (BE)

(73) Assignees: New England Medical Center, Boston, MA (US); University of Mons-Hainaut, Mons (BE)

(*) Notice: Subject to any disclaimer, the term of this patent is extended or adjusted under 35 U.S.C. 154(b) by 723 days.

(21) Appl. No.: 10/185,369

(22) Filed: Jun. 27, 2002

(65) Prior Publication Data

US 2003/0082526 A1    May 1, 2003

Related U.S. Application Data

(60) Provisional application No. 60/301,384, filed on Jun. 27, 2001.

(51) Int. Cl.
    C12Q 1/68        (2006.01)
    G01N 33/50       (2006.01)
(52) U.S. Cl. ............... 435/6; 435/4; 436/63; 436/64
(58) Field of Classification Search .............. 435/4, 435/6; 436/63, 64
    See application file for complete search history.

(56) References Cited

U.S. PATENT DOCUMENTS 6,355,775 B1    3/2002    Nagasawa et al.

OTHER PUBLICATIONS

Shantz and Pegg, Int J of Biochem and Cell Biol., 1999, vol. 31, pp. 107-122.*
McClean and Hill, Eur J of Cancer, 1993, vol. 29A, pp. 2243-2248.*
Fu et al, EMBO Journal, 1996, vol. 15, pp. 4392-4401.*
Hibi, et al., "Methylation pattern of HLTF Gene in Digestive Tract Cancers", *Int. J. Cancer*, 104:433-436 (2003).
International Search Report for PCT/US02/20757, mailed Oct. 20, 2003.
Brummelkamp et al., "A system for Stable Expression of Short Interfering RNAs in Mammalian Cells", Science, 296:550-553 (2002).
Czubayko et al., "Ribozyme-targeting Elucidates a Direct Role of Pleiotrophin in Tumor Growth", J. biol. Chem., 269:21358-21363 (1994).
Ding et al., "Characterization of a Helicase-Like Transcription Factor Invovled in the Expression of the Human Plasminogen Activator Inhibitor-1 Gene", DNA Cell Biol., 15:429-442 (1996).
Ding et al., "Functional Interactions between Sp1 or Sp3 the Helicase-like Transcription Factor Mediate Basal Expression from the Human Plasminogen Activator Inhibitor-1 Gene", J. Biol. Chem., 274:19573-19580 (1999).
GENBANK™ Accession No. AY093185, *Arabidopsis thaliana*, Apr. 21, 2002.
GENBANK™ Accession No. AY093211, *Arabidopsis thaliana*, Apr. 21, 2002.

GENBANK™ Accession No. NM 120595, *Arabidopsis thaliana*, Jan. 10, 2002.
Ghose et al., "Preparation of Antibody-Linked Cytotoxic Agents", Methods in Enzymology, 93:326-327 (1983).
Hicham et al., "A novel high throughput screening assay for HCV NS3 helicase activity", Antiviral Res., 46:181-193 (2000).
Higgins et al., "Fast sensitive multiple sequence alignments on a microcomputer", Cabios 5(2):151-153 (1989).
Kobayashi et al., "Reversal of Drug Sensitivity in Multidrug-Resistant Tumor Cells by an MDR1 (PGY1) Ribozyme", Cancer Res., 54:1271-1275 (1994).
Liang et al., "Differential Dsiplay of Eukaryotic Messenger RNA by Means of the Polymerase Chain Reaction", Science 257:967-971 (1992).
Mahieu et al., "Consturction of a Ribozyme Directed Against Human Interleukin-6 mRNA: Evaluationfo Its Catalytic Activity In Vitro and In Vivo", Blood, 84:3758-3765 (1994).
Marasco et al., "Design, intracellular expression, and activity of a human anti-human immunodeficiency virus type 1gp120 single-chain antibody", Proc. Natl. Acad. Sci. USA 90:7889-7893 (1993).
Marasco et al., Intrabodies: turnign the humoral immune system outside in for intacellular immunization, Gene Therapy, 4:11-15 (1997).
Sullivan et al., "Development of Ribozymes For Gene Therapy", J. Invest. Derm., 103:855-895 (1994).
Sivaraja et al., "High-Throughput Screening Assay for Helicase Enzymes", Anal. Biochem., 265:22-27 (1998).
Zamore et al., "Ancient Pathways Programmed by Small RNAs", Science, 296:1265-1269, 2002.
Sheridan et al., "Cloning of an SNF2/SWI2-related Protein That Binds Specifically to the SPH Motifs of the SV40 Enhancer to the HIV-1 Promoter", J. Bio. Chem. 270(9):4575-4587 (1995).
Moinova et al., "HLTF gene silencing in human colon cancer", PNAS 99(7):4562-4567, 2002.
Mahajan et al., "DNA-dependent adenosine triphosphatase (helicaselike transcription factor) activates β-globin tanscription in K562 cells", Blood, 99(1):348-356 (2002).
Gong, et al., "Developmetnal Regulation of Zbu1, a DNA-Binding Member fo the SWI2/SNF2 Family", Develop. Bio. 183:166-182 (1997).
GENBANK™ Accession No. NM003071, *Homo sapiens*, May 22, 2002.
Hayward-Lester, et al., "Cloning, Characterization, and Steroid-Dependent Posttranscriptional Processing of RUSH-1α and β, Two Uteroglobin Promoter-Binding Proteins", Mol. Endocrinology, 10(11):1335-1349 (1996).

(Continued)

*Primary Examiner*—Larry R Helms
*Assistant Examiner*—Anne L. Holleran
(74) *Attorney, Agent, or Firm*—Mintz, Levin, Cohn, Ferris, Glovsky and Popeo, P.C.; Ingrid A. Beattie

(57) ABSTRACT

The invention is based on the elucidation of a mechanism by which HPV promotes oncogenesis and provides a methods of diagnosing malignant tumors and methods of preventing the development of malignancies or inhibiting tumor growth. A method for diagnosing a neoplasm in a mammal is carried out by measuring the level of helicase-like transcription factor (HLTF) in tissue of the mammal. An increase in the level of HLTF in the tissue compared to the level in a normal control tissue indicates the presence of a neoplasm in the tissue.

7 Claims, 9 Drawing Sheets

OTHER PUBLICATIONS

GENBANK™ Accession No. U66564, Oryctolagus cuniculus, Jun. 3, 1998.

GENBANK™ Accession No. U66565, Oryctolagus cuniculus, Jan. 22, 1997.

Sheridan, et al., "Cloning of an SNF2/SWI2-related Protein That Binds Specifically to the SPH Motifs of the SV40 Enhancer to the HIV-1 Promoter", J. Bio. Chem., 270(9): 4575-4587 (1995).

GENBANK™ Accession No. L34673, Homo sapiens, May 25, 1995.

Zhang, et al., "Molecular cloning and characterization of P113,a mouse SNF2/SWI2-related transcription factor", Gene 202(1-2):31-37 (1997).

GENBANK™ Accession No. NM009210, *Mus musculus*, Sep. 19, 2002.

Database Medline Online, Database Accession No. NLM11029768 (abstract), Jan. 2000.

Hening et al. *Breast Cancer Res. Treat.*, 53(2):121-135 (1999).

* cited by examiner

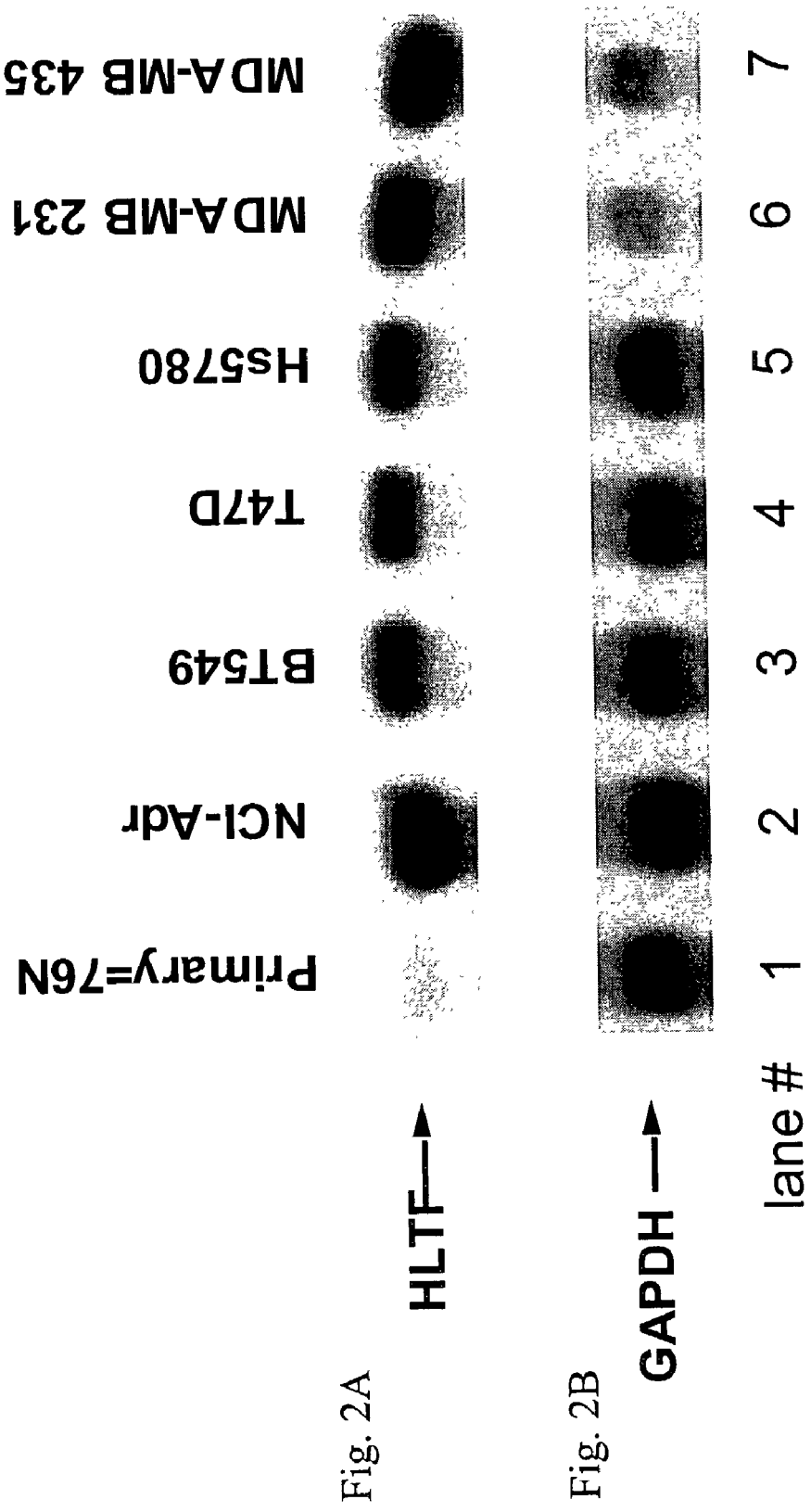

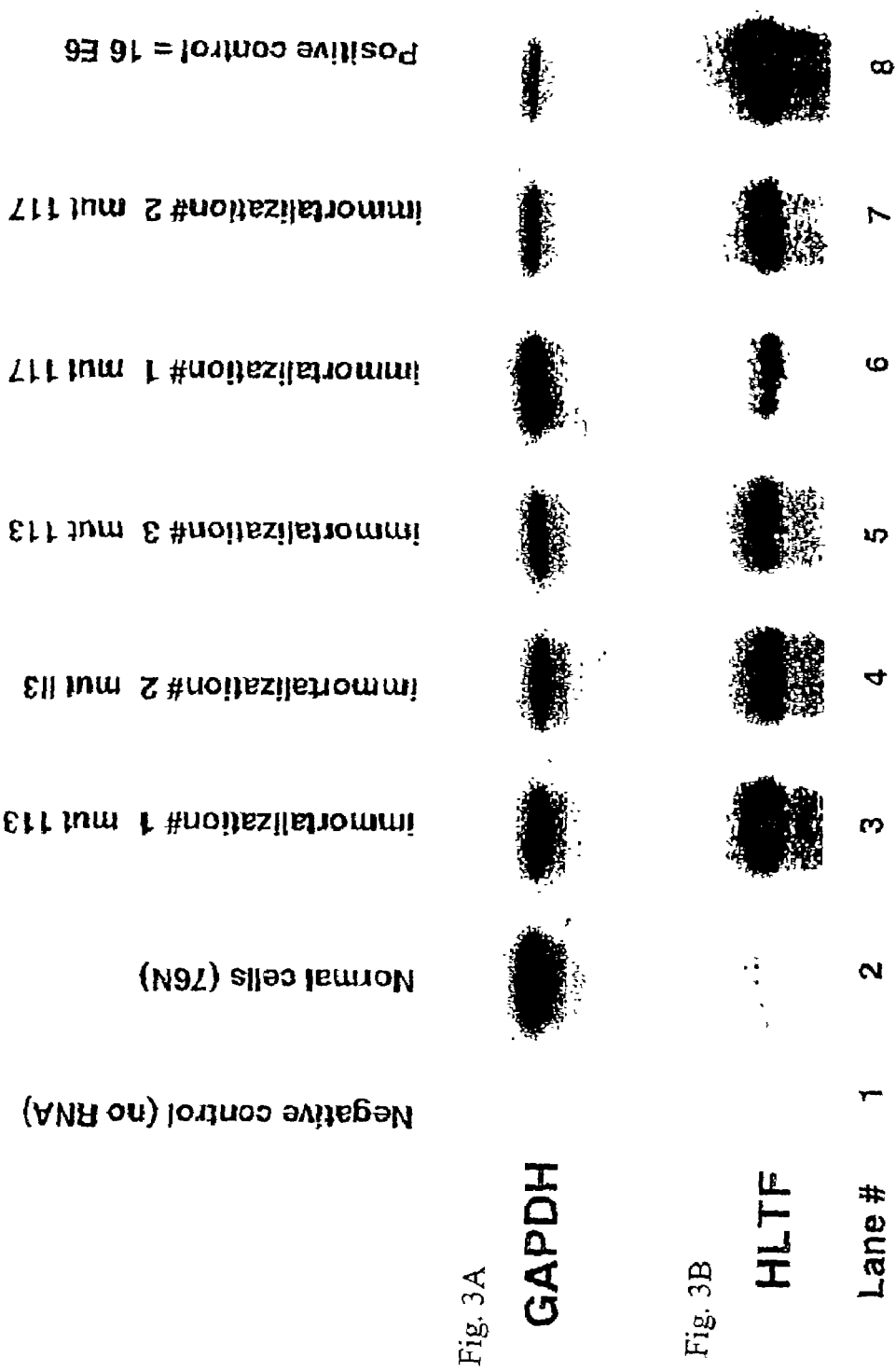

Fig. 6

1    gaattcacgtgactacgcacatcatgtacacactcccgtccacgaccgaccccgctgt t
61   ttattttaatagctacaaagcaggaaatccctgctaaaatgtcctttaacaaactggt t
121  aaacaaacgggtccatccgcacgtggacagttcctcacagtgaagaggaacatgccgtt
181  tataaagcctgcaggcatctcaagggaattacgctgagtcaaaactgccacctccatggg
241  atacgtacgcaacatgctcaaaaagaaagattttcaccccatggcaggggagtggttggg
301  ggttaaggacggtgggggcaggcagctgggggctactgcacgcaccttttactaaagccag
361  tttcctggttctgatggtattggctcagttatgggagactaaccataggggagtgggat
421  gggggaacccggaggctgtgccatctttgccatgcccgagtgtcctgggcaggataatgc (SEQ. ID NO. 8)

Shown in bold are several consensus HLTF binding sites

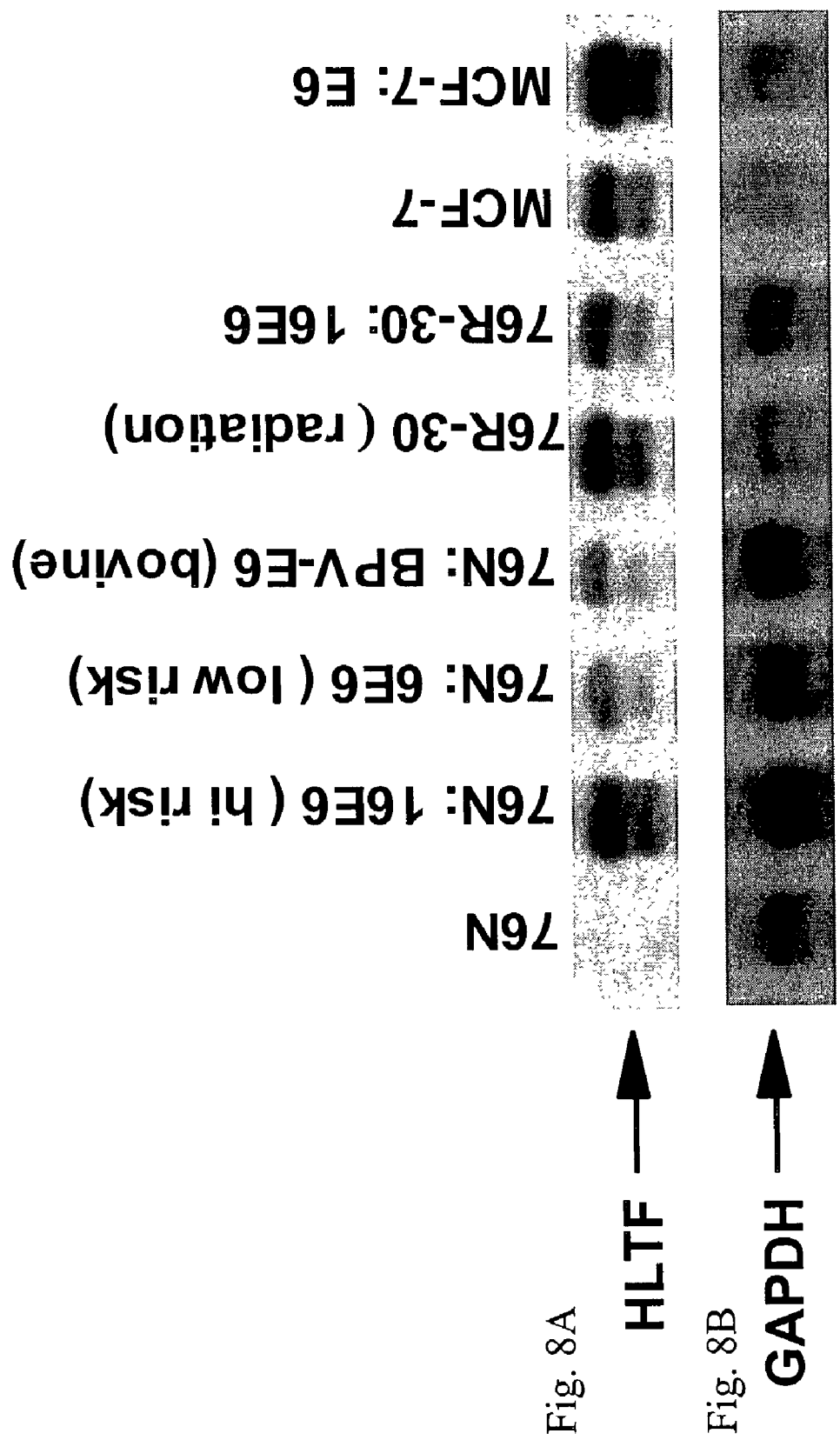
Fig. 8A HLTF
Fig. 8B GAPDH

```
                         SEQUENCE LISTING

<160> NUMBER OF SEQ ID NOS: 10

<210> SEQ ID NO 1
<211> LENGTH: 5
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1 ctgcc                                                               5

<210> SEQ ID NO 2
<211> LENGTH: 5
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2 caccc                                                               5

<210> SEQ ID NO 3
<211> LENGTH: 5
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3 ggcag                                                               5

<210> SEQ ID NO 4
<211> LENGTH: 5
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4 agtgg                                                               5

<210> SEQ ID NO 5
<211> LENGTH: 5
<212> TYPE: DNA
<213> ORGANISM: Artificial Sequence
<220> FEATURE:
<223> OTHER INFORMATION: Description of Artificial Sequence:
      oligonucleotide
```

```
<400> SEQUENCE: 5 ggcag                                                                      5

<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6 agctgg                                                                     6

<210> SEQ ID NO 7
<211> LENGTH: 5
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7 ggctg                                                                      5

<210> SEQ ID NO 8
<211> LENGTH: 480
<212> TYPE: DNA
<213> ORGANISM: Homo sapiens

<400> SEQUENCE: 8
gaattcacgt gactacgcac atcatgtaca cactcccgtc cacgaccgac ccccgctgtt         60
ttattttaat agctacaaag cagggaaatc cctgctaaaa tgtcctttaa caaactggtt        120
aaacaaacgg gtccatccgc acggtggaca gttcctcaca gtgaagagga acatgccgtt        180
tataaagcct gcaggcatct caagggaatt acgctgagtc aaaactgcca cctccatggg        240
atacgtacgc aacatgctca aaagaaaga ttttcacccc atggcagggg agtggttggg         300
ggttaaggac ggtgggggca gcagctgggg gctactgcac gcaccttta ctaaagccag         360 tttcctggtt ctgatggtat tggctcagtt atgggagact aaccataggg gagtggggat        420
gggggaaccc ggaggctgtg ccatctttgc catgcccgag tgtcctgggc aggataatgc        480

<210> SEQ ID NO 9
<211> LENGTH: 5317
<212> TYPE: DNA
<213> ORGANISM: Homo sapiens

<400> SEQUENCE: 9
ttgttgcaga aggagacggc gtcgacgtct gactggactc gcggcgactt acctttcagt         60
cgtgcgctcc tgatccggcg ctcggaattt gtccccggct tcagggctgc ggggcctgga        120
aggaggcgta tcgaggcggc tcgaaaacga tccaggggag ccgaggcgct cctcttgtca        180
tcccactcag cgccatgtcc tggatgttca gagggatcc agtttggaag tacttgcaga         240
ctgtccagta tggagttcat ggaaattttc cacgcctctc atatccaact ttctttccac        300
gttttgaatt ccaagatgtt atccctccag atgactttct aactagtgat gaagaagtag        360
attccgtttt atttggaagt ttgagaggtc atgtggttgg actacgctat tacacgggag        420
tagttaataa taatgaaatg gttgcattac aacgagatcc taataaccct tatgataaga        480
atgcaattaa agtaaacaat gtgaatggaa atcaagttgg ccatttaaag aaagagcttg        540
```

-continued

| | |
|---|---|
| caggtgcttt ggcctatatc atggacaaca aattggcaca aattgaaggg gtagttcctt | 600 |
| ttggtgcaaa caatgctttt accatgcctc tgcatatgac ttttggggga aaagaagaaa | 660 |
| atagaaaagc ggtttcagat cagttgaaga acatggatt taaattgggt cctgcaccaa | 720 |
| aaactttagg attcaatttg gaaagtggtt ggggctctgg aagagctgga ccaagctata | 780 |
| gtatgccagt gcatgctgca gtacagatga caactgaaca gcttaaaaca gaatttgaca | 840 |
| aattgtttga agatttaaaa gaagatgata aaacccatga aatggaacca gctgaggcta | 900 |
| ttgaaacacc actgcttcca catcaaaaac aagctctagc ttggatggtg tcacgggaaa | 960 |
| atagcaaaga acttccacca ttctgggaac agcgaaatga cttatactat aacacaataa | 1020 |
| caaattttc tgagaaggac cgaccagaaa atgtccatgg aggaatttta gctgatgata | 1080 |
| tgggtttggg taaaactctt acggccattg cagtaatcct taccaacttc catgatggca | 1140 |
| gacctcttcc tattgaaaga gttaaaaaga atctactgaa gaaggaatat aatgttaacg | 1200 |
| atgactctat gaaacttgga ggaaacaata ccagtgaaaa ggcagatgga ctaagcaaag | 1260 |
| acgcatctag atgtagtgaa caacccagta tttcagatat caaggagaag agtaagtttc | 1320 |
| gcatgtcaga attgtctagc tcccgcccca aaagaagaaa aactgctgtc cagtacatag | 1380 |
| aaagcagtga ttcagaggaa attgaaacaa gtgaattgcc gcagaaaatg aaaggcaaac | 1440 |
| tgaaaaatgt acagtctgaa actaaaggca gggcgaaagc aggatcttct aaggttatag | 1500 |
| aagatgtggc atttgcatgt gcattaactt catctgttcc tacaacaaaa agaaaatgt | 1560 |
| tgaaaaaggg agcttgtgca gtggaggggt caaagaaaac tgatgttgag gagagaccaa | 1620 |
| gaacaacact gatcatctgt ccgctttctg tgttaagcaa ctggattgac cagtttggac | 1680 |
| aacatataaa atcagatgta cacttgaatt tttatgttta ttatggtcct gatcgtatta | 1740 |
| gagaaccggc cttactttca aaacaggata ttgttttgac tacgtataat atttaactc | 1800 |
| atgactatgg aactaaagga gatagtccat tacatagcat aaggtggcta agagtgatcc | 1860 |
| tggatgaagg acatgccata cgaaatccaa atgctcagca gacaaaagct gtacttgact | 1920 |
| tagaatcaga aagaagatgg ttttgacag gtactccaat ccagaattct ttaaaggact | 1980 |
| tgtggtctct tctttccttt ttaaaactta aaccatttat tgatagagaa tggtggcata | 2040 |
| gaacaataca gcgtcctgtc acaatgggag atgaaggagg acttaggcgt ttacagtccc | 2100 |
| taattaaaaa tattacactt agaagaacaa agacaagcaa aattaaagga aaacctgttt | 2160 |
| tggagttacc agaacgtaaa gtatttattc agcacattac actttcagat gaagagagaa | 2220 |
| agatttatca gtctgtgaaa aatgaaggca gagccactat tggaaggtat tttaatgaag | 2280 |
| ggactgtcct ggcacattat gcagatgtcc tgggtctttt gcttagactg cggcaaattt | 2340 |
| gttgccatac ttaccttctt acaaatgcag tgtcttccaa tggcccctca ggaaatgata | 2400 |
| cacctgaaga actgagaaag aagttaataa ggaagatgaa gttaattctg agctcaggtt | 2460 |
| cagatgagga atgtgcaatt tgcctggatt ctttaacagt tcctgtgata acacattgtg | 2520 |
| cacatgtatt ttgtaaaccc tgtatttgcc aagtcattca gaatgagcag ccacatgcta | 2580 |
| aatgcccttt atgcagaaat gatatacatg aagataattt attagaatgt cctccagaag | 2640 |
| aattagcacg tgacagtgag aaaaagtctg atatggaatg gacatccagt tcaaagatta | 2700 |
| atgcgctaat gcacgcattg actgacttaa gaaagaagaa tcccaacata aaaagtttgg | 2760 |
| ttgtttctca gtttacaaca ttcctgtctt taatagaaat accacttaaa gcctctggat | 2820 |
| ttgtgtttac tcgtttggat ggttccatgg cccaaaagaa aagagttgaa tcaattcagt | 2880 |
| gttttcaaaa cactgaagca ggatctccaa ctataatgct tctgtcctta aaagcaggtg | 2940 |

```
gagttggttt gaatctgtct gcagcttctc gagtgttttt aatggatcca gcctggaatc    3000
ctgctgctga agatcagtgc tttgacagat gccatagact tggtcagaag caagaagtta    3060
tcatcacaaa attcattgta aaggactctg ttgaagaaaa tatgctgaaa atacaaaaca    3120
aaaagagaga acttgcagca ggagcctttg gaactaaaaa accaaatgct gacgaaatga    3180
aacaagccaa aattaatgaa atcagaacat taattgactt ataatttgtg ggattttagt    3240
aaggtcagtt tgattggata cttaagtttt agaaatgaga aaaatacaga gttttagaaa    3300
tgagatctag agaacacgtc ttctaaaagg ggcatatttt atattagtga agaggtatta    3360
ctgacacaat ttcttctata tatgaaccta tttttaatga aacttcaaat agcaataagt    3420
tccgttatat actgtggcct gaaataattt gagaaaaaag gttactttgt tattcagctt    3480
ttcataatat ctatgctgag tattttcacg tatcttccaa gtactcagct ttttcgtatt    3540
tcaaataagg tcagaccttt tatacttttg accaaatagt tattttctat gttggacact    3600
tagttattta ccaaagcctc cgatttgtga tgcagtgttt gtagtccttg taaacaatat    3660
atacagacta tacaagaatt aattttattg ggctttcaaa accatatttt gcattccaga    3720
accaaatctt aaatgagacc aaagtccagg ttagcacagg ttttattttt tcctacagct    3780
acattgagat atagttcaca taaatgactt ggagttttat gttcatgaaa aaattaggga    3840
ttatgttaag agtactattt tttccatttt agttaagtag tactcactc attgtttaaa    3900
tgtaacttgc tgtgtctgag gtataaatat agtctgtggg agtgagaggc aaaccagtcc    3960
tacccaattt gatttgaata ttttaaatta tggaactgct aaatagatat ttctataaat    4020
agataatttt tatttatgta gcttttttg gaagtaactt tataaatttt tataattcag    4080
aagactacta tatgtgagag gcgtgatatc tggatggaag ttgggctgga tgatctccaa    4140
agtcgtttca actcttaaag acatcttaat cctgaatgta aacaattgtt atgtgtttag    4200
aatcagaatt tgattttgaa cttgagtaat tcatccttac agctatctgt agaattagtc    4260
atcttttttc ttttctttt tttttacttt tttgttaata agcaaactta tttgctgcag    4320
aatttgggtt gactcctgag catatttaaa acaaagaagc tagaaattta gcagtcagat    4380
taggtaggtg gttttatttc aaagggaaac tttaatccaa agaaagatta attactctaa    4440
caaacaagag aagcttcatg tttgatgata cagatttaag aatacctgag acttaagagt    4500
gttggaagtc atttgataga aagatgagat cggagacaat gttgtgttat agggcacaca    4560
ttgaaggtat atgccaaatc tctcaccaga taagtccttt tctccctgtg ccgttttctt    4620
gctcaaaggg aacagtgaat tagccagcta gaatcttcct ggtcccttttt tgaggcagta    4680
gcaggtaagg aaagggctga ttttcatcaa aaccaagacc tttctgcagg gatgatagtg    4740
gaataataat gtgggattag cccgctagca ttaggagcag ttgggaagtt acctggtaga    4800
tcaagcatta cacacaaaaa atcaagttga tcagagtatg ggttctccat atagcaatac    4860
ttcagtgaga ttaagtataa acagttttttg gcaaaaaaca acacagtcta ctctttctgc    4920
ttacaaagac aaagccttac aaactcacta tgaaggtaaa gggaggacag cttgcttctt    4980
tgcccagaca tttacaaagt tgtttttaaa acacactcat aagtaagttt ggcaagttgt    5040
ttaaaaaatg tctctttgtt ttgtacagtt ctgttagatg ttgttatatt ttaaaagttt    5100
aatttaaaaa atttaatttg tccttcctaa gaaggataaa tatataaaaa agccactgga    5160
atgaaaactt cctatatgct atgctgttgt cttattatta tatagaaaaa aactttaga    5220
aaaatattga agacattgta ttccacttg tgattcaaac aattttgtgg ttaaaactgg    5280
attttaaatt taaaaatcaa taaaaatttc aaatgtt                             5317
```

<210> SEQ ID NO 10
<211> LENGTH: 1009
<212> TYPE: PRT
<213> ORGANISM: Homo sapiens

<400> SEQUENCE: 10

```
Met Ser Trp Met Phe Lys Arg Asp Pro Val Trp Lys Tyr Leu Gln Thr
  1               5                  10                  15
Val Gln Tyr Gly Val His Gly Asn Phe Pro Arg Leu Ser Tyr Pro Thr
             20                  25                  30
Phe Phe Pro Arg Phe Glu Phe Gln Asp Val Ile Pro Pro Asp Asp Phe
         35                  40                  45
Leu Thr Ser Asp Glu Glu Val Asp Ser Val Leu Phe Gly Ser Leu Arg
     50                  55                  60
Gly His Val Val Gly Leu Arg Tyr Tyr Thr Gly Val Val Asn Asn Asn
 65                  70                  75                  80
Glu Met Val Ala Leu Gln Arg Asp Pro Asn Asn Pro Tyr Asp Lys Asn
                 85                  90                  95
Ala Ile Lys Val Asn Asn Val Asn Gly Asn Gln Val Gly His Leu Lys
            100                 105                 110
Lys Glu Leu Ala Gly Ala Leu Ala Tyr Ile Met Asp Asn Lys Leu Ala
        115                 120                 125
Gln Ile Glu Gly Val Val Pro Phe Gly Ala Asn Asn Ala Phe Thr Met
    130                 135                 140
Pro Leu His Met Thr Phe Trp Gly Lys Glu Glu Asn Arg Lys Ala Val
145                 150                 155                 160
Ser Asp Gln Leu Lys Lys His Gly Phe Lys Leu Gly Pro Ala Pro Lys
                165                 170                 175
Thr Leu Gly Phe Asn Leu Glu Ser Gly Trp Gly Ser Gly Arg Ala Gly
            180                 185                 190
Pro Ser Tyr Ser Met Pro Val His Ala Ala Val Gln Met Thr Thr Glu
        195                 200                 205
Gln Leu Lys Thr Glu Phe Asp Lys Leu Phe Glu Asp Leu Lys Glu Asp
    210                 215                 220
Asp Lys Thr His Glu Met Glu Pro Ala Glu Ala Ile Glu Thr Pro Leu
225                 230                 235                 240
Leu Pro His Gln Lys Gln Ala Leu Ala Trp Met Val Ser Arg Glu Asn
                245                 250                 255
Ser Lys Glu Leu Pro Pro Phe Trp Glu Gln Arg Asn Asp Leu Tyr Tyr
            260                 265                 270
Asn Thr Ile Thr Asn Phe Ser Glu Lys Asp Arg Pro Glu Asn Val His
        275                 280                 285
Gly Gly Ile Leu Ala Asp Asp Met Gly Leu Gly Lys Thr Leu Thr Ala
    290                 295                 300
Ile Ala Val Ile Leu Thr Asn Phe His Asp Gly Arg Pro Leu Pro Ile
305                 310                 315                 320
Glu Arg Val Lys Lys Asn Leu Leu Lys Glu Tyr Asn Val Asn Asp
                325                 330                 335
Asp Ser Met Lys Leu Gly Gly Asn Asn Thr Ser Glu Lys Ala Asp Gly
            340                 345                 350
Leu Ser Lys Asp Ala Ser Arg Cys Ser Glu Gln Pro Ser Ile Ser Asp
        355                 360                 365
Ile Lys Glu Lys Ser Lys Phe Arg Met Ser Glu Leu Ser Ser Ser Arg
    370                 375                 380
```

-continued

```
Pro Lys Arg Arg Lys Thr Ala Val Gln Tyr Ile Glu Ser Ser Asp Ser
385                 390                 395                 400

Glu Glu Ile Glu Thr Ser Glu Leu Pro Gln Lys Met Lys Gly Lys Leu
            405                 410                 415

Lys Asn Val Gln Ser Glu Thr Lys Gly Arg Ala Lys Ala Gly Ser Ser
                420                 425                 430

Lys Val Ile Glu Asp Val Ala Phe Ala Cys Ala Leu Thr Ser Ser Val
            435                 440                 445

Pro Thr Thr Lys Lys Lys Met Leu Lys Lys Gly Ala Cys Ala Val Glu
        450                 455                 460

Gly Ser Lys Lys Thr Asp Val Glu Glu Arg Pro Arg Thr Thr Leu Ile
465                 470                 475                 480

Ile Cys Pro Leu Ser Val Leu Ser Asn Trp Ile Asp Gln Phe Gly Gln
                485                 490                 495

His Ile Lys Ser Asp Val His Leu Asn Phe Tyr Val Tyr Tyr Gly Pro
            500                 505                 510

Asp Arg Ile Arg Glu Pro Ala Leu Leu Ser Lys Gln Asp Ile Val Leu
        515                 520                 525

Thr Thr Tyr Asn Ile Leu Thr His Asp Tyr Gly Thr Lys Gly Asp Ser
530                 535                 540

Pro Leu His Ser Ile Arg Trp Leu Arg Val Ile Leu Asp Glu Gly His
545                 550                 555                 560

Ala Ile Arg Asn Pro Asn Ala Gln Gln Thr Lys Ala Val Leu Asp Leu
                565                 570                 575

Glu Ser Glu Arg Arg Trp Val Leu Thr Gly Thr Pro Ile Gln Asn Ser
            580                 585                 590

Leu Lys Asp Leu Trp Ser Leu Leu Ser Phe Leu Lys Leu Lys Pro Phe
        595                 600                 605

Ile Asp Arg Glu Trp Trp His Arg Thr Ile Gln Arg Pro Val Thr Met
610                 615                 620

Gly Asp Glu Gly Gly Leu Arg Arg Leu Gln Ser Leu Ile Lys Asn Ile
625                 630                 635                 640

Thr Leu Arg Arg Thr Lys Thr Ser Lys Ile Lys Gly Lys Pro Val Leu
                645                 650                 655

Glu Leu Pro Glu Arg Lys Val Phe Ile Gln His Ile Thr Leu Ser Asp
            660                 665                 670

Glu Glu Arg Lys Ile Tyr Gln Ser Val Lys Asn Glu Gly Arg Ala Thr
        675                 680                 685

Ile Gly Arg Tyr Phe Asn Glu Gly Thr Val Leu Ala His Tyr Ala Asp
690                 695                 700

Val Leu Gly Leu Leu Leu Arg Leu Arg Gln Ile Cys Cys His Thr Tyr
705                 710                 715                 720

Leu Leu Thr Asn Ala Val Ser Ser Asn Gly Pro Ser Gly Asn Asp Thr
                725                 730                 735

Pro Glu Glu Leu Arg Lys Lys Leu Ile Arg Lys Met Lys Leu Ile Leu
            740                 745                 750

Ser Ser Gly Ser Asp Glu Glu Cys Ala Ile Cys Leu Asp Ser Leu Thr
        755                 760                 765

Val Pro Val Ile Thr His Cys Ala His Val Phe Cys Lys Pro Cys Ile
770                 775                 780

Cys Gln Val Ile Gln Asn Glu Gln Pro His Ala Lys Cys Pro Leu Cys
785                 790                 795                 800
```

-continued

```
Arg Asn Asp Ile His Glu Asp Asn Leu Leu Glu Cys Pro Pro Glu Glu
            805                 810                 815

Leu Ala Arg Asp Ser Glu Lys Lys Ser Asp Met Glu Trp Thr Ser Ser
            820                 825                 830

Ser Lys Ile Asn Ala Leu Met His Ala Leu Thr Asp Leu Arg Lys Lys
            835                 840                 845

Asn Pro Asn Ile Lys Ser Leu Val Val Ser Gln Phe Thr Thr Phe Leu
    850                 855                 860

Ser Leu Ile Glu Ile Pro Leu Lys Ala Ser Gly Phe Val Phe Thr Arg
865                 870                 875                 880

Leu Asp Gly Ser Met Ala Gln Lys Lys Arg Val Glu Ser Ile Gln Cys
            885                 890                 895

Phe Gln Asn Thr Glu Ala Gly Ser Pro Thr Ile Met Leu Leu Ser Leu
            900                 905                 910

Lys Ala Gly Gly Val Gly Leu Asn Leu Ser Ala Ala Ser Arg Val Phe
            915                 920                 925

Leu Met Asp Pro Ala Trp Asn Pro Ala Ala Glu Asp Gln Cys Phe Asp
    930                 935                 940

Arg Cys His Arg Leu Gly Gln Lys Gln Glu Val Ile Ile Thr Lys Phe
945                 950                 955                 960

Ile Val Lys Asp Ser Val Glu Glu Asn Met Leu Lys Ile Gln Asn Lys
            965                 970                 975

Lys Arg Glu Leu Ala Ala Gly Ala Phe Gly Thr Lys Lys Pro Asn Ala
            980                 985                 990

Asp Glu Met Lys Gln Ala Lys Ile Asn Glu Ile Arg Thr Leu Ile Asp
        995                 1000                1005

Leu
```

DIAGNOSIS AND TREATMENT OF CANCER

This application claims priority to provisional application U.S. Ser. No. 60/301,384, filed on Jun. 27, 2001, the entire contents of which is hereby incorporated by reference.

BACKGROUND OF THE INVENTION

The invention relates to cancer therapy.

Human papillomavirus (HPV) is one of the most common causes of sexually transmitted disease (STD) in the United States. It is estimated that as many as 40 million Americans are infected with HPV, and the incidence of this disease appears to be increasing. More than 100 types of HPV have been identified. HPVs are DNA viruses that infect the proliferative layer of the dermis and cause hyperproliferative lesions (warts), which occasionally progress to full malignancy. HPV infection can lead to genital warts and has been closely associated with the development of cervical cancer and other cancers. The high-risk HPV types are associated with cancers of the anogenital epithelium. HPV oncogenic function has been mapped to the early viral genes E6 and E7, but mechanisms of oncogenesis remain undefined.

SUMMARY OF THE INVENTION

The invention is based on the elucidation of a mechanism by which HPV promotes oncogenesis and provides methods of diagnosing malignant tumors as well as methods of preventing the development of malignancies or inhibiting tumor growth.

A method for diagnosing a neoplasm, e.g., breast and genital cancers, in a mammal is carried out by measuring the level of helicase-like transcription factor (HLTF) in bodily tissue or fluid of the mammal, e.g. a human patient. An increase in the level of HLTF, or isoforms thereof, in the test tissue compared to the level in a normal control tissue or fluid indicates the presence of a neoplasm in the tissue. The level of HLTF is determined by detecting a HLTF transcript or by detecting a HLTF gene product. The tissue is any tissue suspected of containing a malignant tumor, e.g., breast or skin tissue or tissue from any anatomical location, which contains an HPV-containing lesion. One method of detecting the presence of a malignant tumor or a predisposition to developing a tumor includes contacting a test sample of nucleic acid molecules obtained from the tissue with a nucleic acid probe which hybridizes under stringent conditions to a HLTF nucleic acid molecule. Preferably, the tissue sample contains an epithelial cell. The level of binding of the HLTF-specific probe is determined. An increase in binding compared to a normal control level of binding indicates the presence of a malignant tumor or a predisposition to developing such a tumor. HLTF levels are also determined using reagents, which detect HLTF gene products, e.g., HLTF-specific antibodies.

In addition to diagnostic methods, the invention includes therapeutic methods. For example, a method of inhibiting HPV-mediated (or HPV-independent) carcinogenesis of a cell is carried out by reducing the amount of HLTF (or isoforms thereof) in a target cell. The target cell is one which is malignant or suspected of becoming so, e.g., an HPV-infected cell. A reduction in HLTF in a target cell, e.g., an HPV-infected cell, inhibits carcinogenesis. By carcinogenesis is meant progression from a non-tumor cell to a tumor cell. The term also encompasses progression of a benign tumor cell to a malignant tumor. Methods of reducing the amount of HLTF in a cell include the step of contacting the cell with an HLTF antisense compound or an HLTF-specific ribozyme. Non-malignant tumors, e.g., warts, are also treated as described herein. For example, an HLTF is locally administered to a wart (e.g., as a topical cream or directly injected into a lesion) to kill HPV-infected cells or inhibit the growth of HPV-infected cells and to retard the growth of the lesion.

HPV-mediated or HPV-independent carcinogenesis of a cell is also inhibited by contacting the cell with a compound which inhibits binding of endogenous HLTF to a telomerase reverse transcriptase (TERT) promoter. For example, the compound is an oligonucleotide containing a nucleotide sequence selected from the group consisting of ctgcc (SEQ ID NO: 1), caccc (SEQ ID NO: 2) ggcag (SEQ ID NO: 3), agtgg (SEQ ID NO: 4), ggcag (SEQ ID NO: 5) agctgg (SEQ ID NO: 6), ggctg (SEQ ID NO: 7). The oligonucleotide binds to endogenous HLTF thereby preventing endogenous HLTF from binding to an intact hTERT promoter region. The compound binds to an hTERT promoter region (e.g., a region of the promoter containing the nucleotide sequence of SEQ ID NO:8), thereby inhibiting endogenous HLTF from binding and transactivating the hTERT promoter. Other examples of compounds, which inhibit HPV-mediated (or HPV-independent) carcinogenesis, include polypeptides (e.g., HLTF fragments) which binds to nucleic acid sequences such as SEQ ID NO: 8 or an HLTF binding site of the promoter such as ctgcc (SEQ ID NO:1), caccc (SEQ ID NO:2) ggcag (SEQ ID NO:3), agtgg (SEQ ID NO:4), ggcag (SEQ ID NO:5) agctgg (SEQ ID NO: 6), ggctg (SEQ ID NO:7), but do not transactivate the hTERT promoter. The invention also includes a fragment, which does not bind to an hTERT promoter.

Inhibitory compounds include fragments of HLTF, which bind to an hTERT promoter region, but do not transactivate hTERT promoter and peptide mimetics thereof. For example, an inhibitory HLTF fragment includes amino acids 1-206 or amino acids 1-286 (and lacks some or all of the remainder of the naturally-occurring HLTF sequence). The amino acid sequence of a naturally-occurring HLTF is shown in Table 1 (SEQ ID NO: 10).

A substantially pure HLTF polypeptide is preferably obtained by expression of a recombinant nucleic acid encoding the polypeptide or by chemically synthesizing the protein. A polypeptide or protein is substantially pure when it is separated from those contaminants which accompany it in its natural state (proteins and other naturally-occurring organic molecules). Typically, the polypeptide is substantially pure when it constitutes at least 60%, by weight, of the protein in the preparation. Preferably, the protein in the preparation is at least 75%, more preferably at least 90%, and most preferably at least 99%, by weight, HLTF Purity is measured by any appropriate method, e.g., column chromatography, polyacrylamide gel electrophoresis, or HPLC analysis. Accordingly, substantially pure polypeptides include recombinant polypeptides derived from a eucaryote but produced in *E. coli* or another procaryote, or in a eucaryote other than that from which the polypeptide was originally derived.

The invention includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic makes the resulting peptide more stable and thus more useful as a therapeutic. Such mimetics, and methods of incorporating them into peptides, are well known in the art. Similarly, the replacement of an L-amino acid residue is a standard way of rendering the peptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides enhances passage of the peptide through the hydrophobic cellular membrane and into the cell.

The invention also encompasses a kit for detecting the amount of HLTF in a biological sample. The kit contains a labeled compound for detecting HLTF protein or nucleic acid (e.g., mRNA or a monoclonal antibody) in a biological sample. Optionally, the kit contains a means for determining the amount of HLTF in the sample and means for comparing the amount of HLTF in the sample with a standard control value. The components of the kit are packaged together in a suitable container. The kit includes instructions for using the components to detect HLTF protein or nucleic acid.

For diagnostic purposes, a bodily tissue sample is obtained from an individual suspected of having a malignant tumor or at risk of developing a malignant tumor and tested as described above to determine the level of HLTF in the sample. A test value that is at least 10% greater than the normal control value indicates that the sample contains a malignant tumor. Preferably, the test sample value is at least 25%, 50%, 100% or 200% greater than a normal control value (or a value derived from a non-malignant tumor). For prognostic purposes, e.g., to evaluate a response to therapy, HLTF levels are measured over time. For example, a baseline level is taken prior to the start of therapy and then over the course of therapy (and optionally after therapy is concluded). An increase in HLTF values over time indicates a less favorable prognosis (i.e., an increase in malignancy or unfavorable response to therapy), whereas a reduction in HLTF values over time indicate a more favorable prognosis (e.g., a decrease in malignancy or favorable response to therapy).

Nucleotide and/or amino acid sequences described herein may vary from the reference sequence but still retain one or biological activities of the reference composition. For example, an HLTF polypeptide is at least 75%, 80%, 90%, 95%, or 99% identical to the amino acid sequence shown in Table 1 (SEQ ID NO: 10). Nucleotide and amino acid comparisons described herein are carried out using the Lasergene software package (DNASTAR, Inc., Madison, Wis.). The MegAlign module used was the Clustal V method (Higgins et al., 1989, CABIOS 5(2):151–53). The parameter used are gap penalty 10 and gap length penalty 10.

Hybridization, e.g., for diagnostic purposes, is carried out using standard techniques, such as those described in Ausubel et al. (*Current Protocols in Molecular Biology*, John Wiley & Sons, 1989). "High stringency" refers to nucleic acid hybridization and wash conditions characterized by high temperature and low salt concentration (wash conditions of 65° C. at a salt concentration of 0.1×SSC). "Low" to "moderate" stringency refers to DNA hybridization and wash conditions characterized by low temperature and high salt concentration (wash conditions of less than 60° C. at a salt concentration of 1.0×SSC). For example, high stringency conditions include hybridization at 42° C. in the presence of 50% formamide; a first wash at 65° C. in the presence of 2×SSC and 1% SDS; followed by a second wash at 65° C. in the presence of 0.1%×SSC. Lower stringency conditions suitable for detecting DNA sequences having about 50% sequence identity to an HAAH gene sequence are detected by, e.g., hybridization at about 42° C. in the absence of formamide; a first wash at 42° C., 6×SSC, and 1% SDS; and a second wash at 50° C., 6×SSC, and 1% SDS.

The diagnostic method has advantages over existing diagnostic methods. For example, the method allows very early detection of malignancy, e.g., prior to overt physical symptoms or histological changes. Another advantage is that the method is objective, i.e., a determination of malignancy is based on measured values which are compared to standard control values, rather than subjective viewing of histological samples by a individual such as a clinical pathologist.

Methods of preventing senescence are also within the invention. Such methods include a step of enhancing HLTF activity, e.g., TERT promoter transactivation, in cells to promote viability and longevity. Augmenting HLTF expression or activity allows production of permanent, immortal cell lines. Cells containing heterologous HLTF sequences or cells which have been modified for increased HLTF activity or to express increased levels of HLTF, are useful as drug discovery tools, or for replacing diseased human tissues, e.g., by transplanting normal immortal cells. Plant cells are immortalized using a plant HLTF (e.g., an Arabidopsis HLTF polypeptide or nucleic acid such as those described in GENBANK™ NM 120595, AY093185, or AY093211). Such immortalized plant cells are useful for production of proteins (e.g., food products or therapeutic compositions) by growing the cells in a controlled environment (e.g., a fermentor), thereby reducing the risk of release of genetically modified plants or cells into the environment.

Other features and advantages of the invention will be apparent from the following description of the preferred embodiments thereof, and from the claims.

BRIEF DESCRIPTION OF THE DRAWINGS

FIGS. 2A–B are photographs of an electrophoretic gel showing that HLTF expression is induced in breast cancers. HLTF expression was measured in 40 ug total RNA in 76N cells (lane 1 or in six commercially available breast cancer lines. Significant induction of HLTF expression over primary cell levels was observed in all cancer lines (lanes 2–8). FIG. 2A shows HLTF expression, and FIG. 2B shows GAPDH expression. RNAse protection assay using HLTF and GAPDH (loading control) probes. Lane 1 is normal primary breast cell strain 76N. Lanes 2–7 are breast cancer derived cell lines.

FIGS. 3A–B are photographs of electrophoretic gels showing that HLTF is induced immortal MECs that express p53. HLTF expression was measured in normal 76N MECs (lane 2) and 76N MECs immortalized using E6 mutants that are unable to promote p53 degradation (lanes 3–8). Three separately immortalized lines were tested. "113" referes to a Y54H mutation, i.e., tyrosine 54 in HPV 16 E6 protein mutated to a histidine. "117" refers to a F2V mutation in 16 E6, i.e., phenylalanine to valine. Equal RNA loading was confirmed by assaying equal amounts of RNA for protection of a probe for the constitutively expressed GAPDH mRNA (top row). HLTF expression is barely detectable in 76N cells (lane 2) but strongly expressed in immortalized cells (16E6 cells=positive control.

FIGS. 4A–B are photomicrographs showing that introduction of HLTF into MECs prolonged MEC lifespan but did not induce MEC immortalization. FIG. 4A shows that dn-p53 R248W does not immortalize 76N cells. FIG. 4B shows that HLTF cooperates with p53 R248W to immortalize MECs. Endogenous p53 in MECs was inactivated by transfecting 76N cells with the dominant-negative p53 (dn-p53) mutant R248W). The transfected cells were seeded and serially passaged in the growth-factor deficient medium D2 which selects for immortal cells. By passage 3 (P-3), the cells transfected with dn-p53 (R248W) had succumbed in D2 medium (FIG. 4A). In contrast, cells with immortal morphology were distinguished in dishes that had been co-transfected with dn-p53 plus full-length HLTF, as well as in dishes transfected with dn-p53 plus small-HLTF (a representative sample is shown in FIG. 4B). Over successive passages, these acquired a more normal morphology and looked similar to 76N cells by immortalized by HPV-16 E6 alone.

FIG. 6 is a diagram of the a TERT promoter region. HLTF binds to a 480 nucleotide region of the TERT promoter (SEQ ID NO: 8). Consensus HLTF binding sites are shown in bold type.

FIGS. 8A–B are photographs of an electrophoretic gel showing that HLTF is expressed at high levels in immortal breast cells. Data from RPA using HLTF is shown in FIG. 8A, and data using GAPDH RNA loading control probe is shown in FIG. 8B. RNA from normal primary breast cells 76N (lane 1), 76N immortalized by HPV 16 E6, HPV 6 E6 or BPV E6 (lanes 2–4), 76N cells immortalized by radiation-76R30 alone or after transfection with HPV 16 E6 (lanes 5, 6); human breast cancer cells MCF-7 alone or transfected with HPV 16 E6 (lanes 7,8)

DETAILED DESCRIPTION

Figure 1:
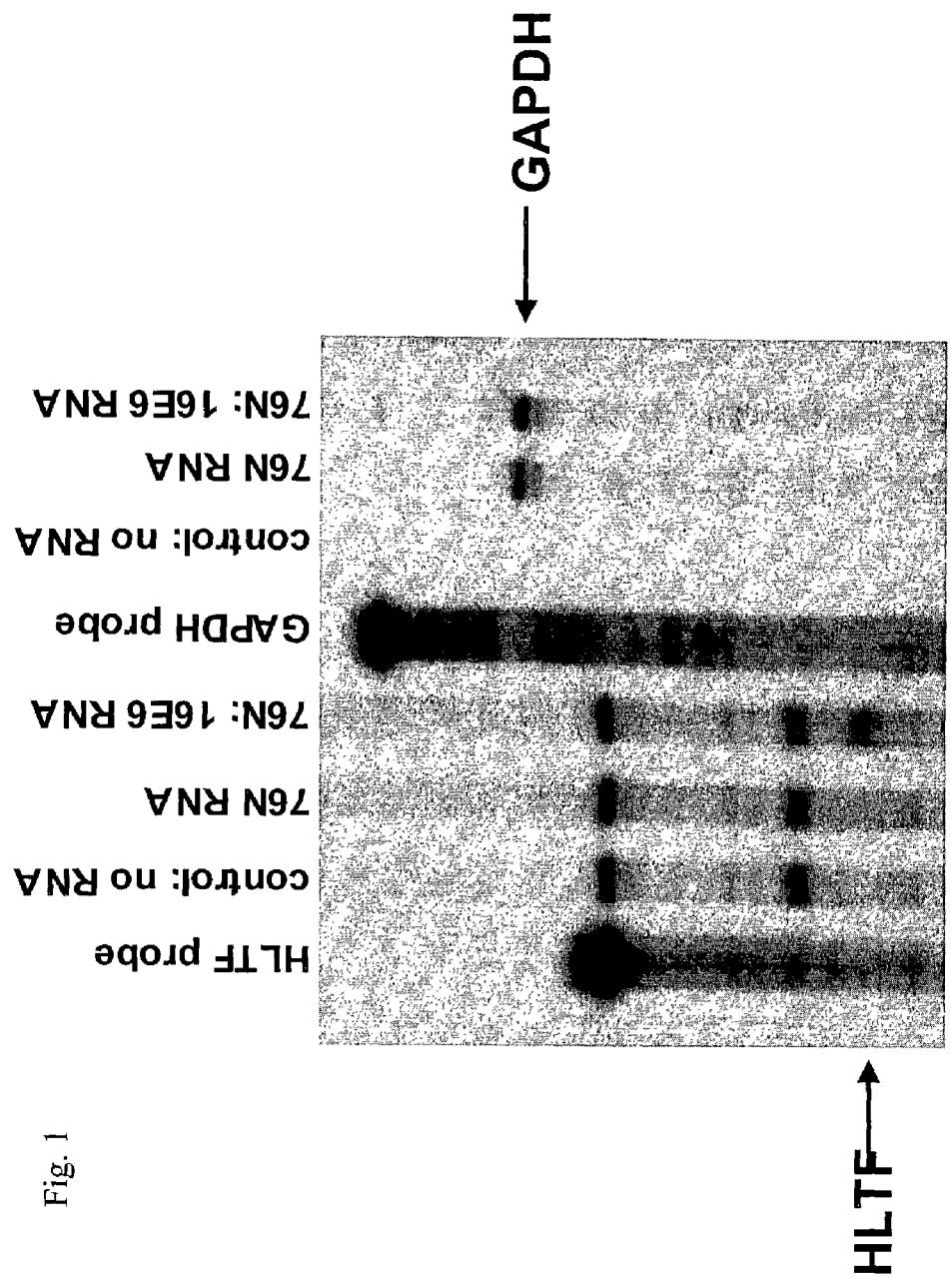
FIG. 1 is a photograph of an electrophoretic gel showing that HLTF expression is induced in immortal cells using an RNAse protection assay. HLTF was found to be differentially expressed in normal and E6-immortalized mammary epithelial cells (MECs) 40 ug of total RNA from primary MEC 76N cells or E6-immortalized cells (76:E6) was assayed for expression of HLTF or GAPDH using a ribonuclease protection assay (RPA). Protected fragments were observed at the expected oppositions for GAPDH after hybridization with 76N RNA (lane 7) or 76:E6 RNA (lane 8). In contrast no signal was observed for HLTF after hybridization to 76N RNA (lane 3), whereas a protected fragment was observed after incubation with 76:E6 RNA (lane 4). Lane 4 shows the HLTF specific band in human breast cells immortalized by HPV 16 E6 but not in normal breast cell strain 76N (lane 3). RNAse protection with GAPDH probe as RNA loading control.

HLTF is a gene that displays motifs of the SWI/SNF family of global transcriptional activators and binds to the promoters of various genes. Expression of HLTF is increased in mammary cells that have undergone immortalization, an early stage in the progression to cancer. The HLTF DNA sequence is used as a predictive diagnostic marker to identify lesions before the onset of full malignancy. HLTF overexpression in conjunction with inactivation of cellular p53 induces MEC immortalization. HLTF sequences (e.g., antisense compounds) and antibodies that bind to an HLTF gene product are useful as therapeutic anticancer agents that modulate the activity of HLTF in vivo.

TABLE 1

HLTF amino acid sequence

1
MSWMFKRDPVWKYLQTVQYGVHGNFPRLSYPTFFPRFEFQDVIPPDD

FLTSDEEVDSVLFGSLRGHVVGLRYYTGVVNNNEMVALQRDPNNPYDKNA

IKVNNVNGNQVGHLKKELAGALAYIMDNKLAQIEGVVPFGANNAFTMPLH

MTFWGKEENRKAVSDQLKKHGFKLGPAPKTLGFNLESGWGSGRAGPSYSM

PVHAAVQMTTEQLKTEFDKLFEDLKEDDKTHEMEPAEAIETPLLPHQKQA

LAWMVSRENSKELPPFWEQRNDLYYNTITNFSEKDRPENVHGGILADDMG

LGKTLTAIAVILTNFHDGRPLPIERVKKNLLKKEYNVNDDSMKLGGNNTS

EKADGLSKDASRCSEQPSISDIKEKSKFRMSELSSSRPKRRKTAVQYIES

SDSEEIETSELPQKMKGKLKNVQSETKGRAKAGSSKVIEDVAFACALTSS

VPTTKKKMLKKGACAVEGSKKTDVEERPRTTLIICPLSVLSNWIDQFGQH

IKSDVHLNFYVYYGPDRIREPALLSKQDIVLTTYNILTHDYGTKGDSPLH

SIRWLRVILDEGHAIRNPNAQQTKAVLDLESERRWVLTGTPIQNSLKDLW

SLLSFLKLKPFIDREWWHRTIQRPVTMGDEGGLRRLQSLIKNITLRRTKT

SKIKGKPVLELPERKVFIQHITLSDEERKIYQSVKNEGRATIGRYFNEGT

VLAHYADVLGLLLRLRQICCHTYLLTNAVSSNGPSGNDTPEELRKKLIRK

MKLILSSGSDEECAICLDSLTVPVITHCAHVFCKPCICQVIQNEQPHAKC

PLCRNDIHEDNLLECPPEELARDSEKKSDMEWTSSSKINALMHALTDLRK

KNPNIKSLVVSQFTTFLSLIEIPLKASGFVFTRLDGSMAQKKRVESIQCF

QNTEAGSPTIMLLSLKAGGVGLNLSAASRVFLMDPAWNPAAEDQCFDRCH

RLGQKQEVIITKFIVKDSVEENMLKIQNKKRELAAGAFGTKKPNADEMKQ

AKINEIRTLIDL (SEQ ID NO:10; GENBANK ACCESSION NO: NM 003071;
"1" indicates first amino acid of HLTF; bold
"M" indicates first amino acid of an HLTF small
isoform)

TABLE 2

HLTF nucleotide sequence (SEQ ID NO:9; GENBANK ACCESSION NO: NM 003071)

```
   1 ttgttgcaga aggagacggc gtcgacgtct gactggactc gcggcgactt acctttcagt
  61 cgtgcgctcc tgatccggcg ctcggaattt gtccccggct tcagggctgc ggggcctgga
 121 aggaggcgta tcgaggcggc tcgaaaacga tccaggggag ccgaggcgct cctcttgtca
 181 tcccactcag cgccatgtcc tggatgttca gagggatcca gtttggaag tacttgcaga
 241 ctgtccagta tggagttcat ggaaattttc cacgcctctc atatccaact ttctttccac
 301 gttttgaatt ccaagatgtt atccctccag atgactttct aactagtgat gaagaagtag
 361 attccgtttt atttggaagt ttgagaggtc atgtggttgg actacgctat tacacgggag
 421 tagttaataa taatgaaatg gttgcattac aacgagatcc taataaccct tatgataaga
 481 atgcaattaa agtaaacaat gtgaatggaa atcaagttgg ccatttaaag aaagagcttg
 541 caggtgcttt ggcctatatc atggacaaca aattggcaca aattgaaggg gtagttcctt
 601 ttggtgcaaa caatgctttt accatgcctc tgcatatgac tttttgggga aaagaagaaa
 661 atagaaaagc ggtttcagat cagttgaaga acatggatt taaattgggt cctgcaccaa
 721 aaactttagg attcaatttg gaaagtggtt ggggctctgg aagagctgga ccaagctata
 781 gtatgccagt gcatgctgca gtacagatga caactgaaca gcttaaaaca gaatttgaca
 841 aattgtttga agatttaaaa gaagatgata aaacccatga aatggaacca gctgaggcta
 901 ttgaaacacc actgcttcca catcaaaaac aagctctagc ttggatggtg tcacgggaaa
 961 atagcaaaga acttccacca ttctgggaac agcgaaatga cttatactat aacacaataa
1021 caaatttttc tgagaaggac cgaccagaaa atgtccatgg aggaatttta gctgatgata
1081 tgggtttggg taaaactctt acggccattg cagtaatcct taccaacttc catgatggca
1141 gacctcttcc tattgaaaga gttaaaaaga atctactgaa gaaggaatat aatgttaacg
1201 atgactctat gaaacttgga ggaaacaata ccagtgaaaa ggcagatgca ctaagcaaag
12601 acgcatctag atgtagtgaa caacccagta tttcagatat caaggagaag agtaagtttc
1321 gcatgtcaga attgtctagc tcccgcccca aaagaagaaa aactgctgtc cagtacatag
1381 aaagcagtga ttcagaggaa attgaaacaa gtgaattgcc gcagaaaatg aaaggcaaac
1441 tgaaaaatgt acagtctgaa actaaaggca gggcgaaagc aggatcttct aaggttatag
1501 aagatgtggc atttgcatgt gcattaactt catctgttcc tacaacaaaa agaaaatgt
1561 tgaaaaaggg agcttgtgca gtggagggt caaagaaaac tgatgttgag gagagaccaa
1621 gaacaacact gatcatctgt ccgctttctg tgttaagcaa ctggattgac cagtttggac
1681 aacatataaa atcagatgta cacttgaatt tttatgttta ttatggtcct gatcgtatta
1741 gagaaccggc cttactttca aaacaggata ttgttttgac tacgtataat attttaactc
1801 atgactatgg aactaaagga gatagtccat acatagcat aaggtggcta agagtgatcc
1861 tggatgaagg acatgccata cgaaatccaa atgctcagca gacaaaagct gtacttgact
1921 tagaatcaga aagaagatgg gttttgacag gtactccaat ccagaattct ttaaaggact
1981 tgtggtctct tctttccttt ttaaaactta accattat tgatagagaa tggtggcata
2041 gaacaataca gcgtcctgtc acaatgggag atgaaggagg acttaggcgt ttacagtccc
2101 taattaaaaa tattacactt agaagaacaa agacaagcaa aattaaagga aaacctgttt
2161 tggagttacc agaacgtaaa gtatttattc agcacattac actttcagat gaagagagaa
2221 agatttatca gtctgtgaaa aatgaaggca gagccactat tggaaggtat tttaatgaag
```

TABLE 2-continued

| HLTF nucleotide sequence |

```
2281 ggactgtcct ggcacattat gcagatgtcc tgggtctttt gcttagactg cggcaaattt
2341 gttgccatac ttaccttctt acaaatgcag tgtcttccaa tggcccctca ggaaatgata
2401 cacctgaaga actgagaaag aagttaataa ggaagatgaa gttaattctg agctcaggtt
2461 cagatgagga atgtgcaatt tgcctggatt ctttaacagt tcctgtgata acacattgtg
2521 cacatgtatt ttgtaaaccc tgtatttgcc aagtcattca gaatgagcag ccacatgcta
2581 aatgcccttt atgcagaaat gatatacatg aagataattt attagaatgt cctccagaag
2641 aattagcacg tgacagtgag aaaaagtctg atatggaatg gacatccagt tcaaagatta
2701 atgcgctaat gcacgcattg actgacttaa gaagaagaa tcccaacata aaaagtttgg
2761 ttgtttctca gtttacaaca ttcctgtctt aatagaaat accacttaaa gcctctggat
2821 ttgtgtttac tcgtttggat ggttccatgg cccaaaagaa aagagttgaa tcaattcagt
2881 gttttcaaaa cactgaagca ggatctccaa ctataatgct tctgtcctta aaagcaggtg
2941 gagttggttt gaatctgtct gcagcttctc gagtgttttt aatggatcca gcctggaatc
3001 ctgctgctga agatcagtgc tttgacagat gccatagact tggtcagaag caagaagtta
3061 tcatcacaaa attcattgta aaggactctg ttgaagaaaa tatgctgaaa atacaaaaca
3121 aaaagagaga acttgcagca ggagcctttg gaactaaaaa accaaatgct gacgaaatga
3181 aacaagccaa aattaatgaa atcagaacat taattgactt ataatttgtg ggattttagt
3241 aaggtcagtt tgattggata cttaagtttt agaaatgaga aaaatacaga gttttagaaa
3301 tgagatctag agaacacgtc ttctaaaagg ggcatatttt atattagtga agaggtatta
3361 ctgacacaat ttcttctata tatgaaccta ttttttaatga aacttcaaat agcaataagt
3421 tccgttatat actgtggcct gaaataattt gagaaaaaag gttactttgt tattcagctt
3481 ttcataatat ctatgctgag tattttcacg tatcttccaa gtactcagct ttttcgtatt
3541 tcaaataagg tcagaccttt tatactttg accaaatagt tattttctat gttggacact
3601 tagttattta ccaaagcctc cgatttgtga tgcagtgttt gtagtccttg taaacaatat
3661 atacagacta tacaagaatt aattttattg ggctttcaaa aaccatattt gcattccaga
3721 accaaatctt aaatgagacc aaagtccagg ttagcacagg tttttatttt tcctacagct
3781 acattgagat atagttcaca taaatgactt ggagttttat gttcatgaaa aaattaggga
3841 ttatgttaag agtactattt tttccatttt agttaagtag tactacactc attgtttaaa
3901 tgtaacttgc tgtgtctgag gtataaatat agtctgtggg agtgagaggc aaaccagtcc
3961 tacccaattt gatttgaata ttttaaatta tggaactgct aaatagatat ttctataaat
4021 agataatttt tatttatgta gctttttttg gaagtaactt tataaatttt tataattcag
4081 aagactacta tatgtgagag gcgtgatatc tggatggaag ttgggctgga tgatctccaa
4141 agtcgtttca actcttaaag acatcttaat cctgaatgta acaattgtt atgtgtttag
4201 aatcagaatt tgattttgaa cttgagtaat tcatccttac agctatctgt agaattagtc
4261 atcttttttc ttttctttt tttttacttt tttgttaata gcaaacttta tttgctgcag
4321 aatttgggtt gactcctgag catatttaaa acaaagaagc tagaaattta gcagtcagat
4381 taggtaggtg gttttatttc aaagggaaac tttaatccaa agaaagatta attactctaa
4441 caaacaagag aagcttcatg tttgatgata cagatttaag aatacctgag acttaagagt
4501 gttggaagtc atttgataga aagatgagat cggagacaat gttgtgttat agggcacaca
4561 ttgaaggtat atgccaaatc tctcaccaga taagtccttt tctccctgtg ccgttttctt
```

TABLE 2-continued

HLTF nucleotide sequence

```
4621 gctcaaggg aacagtgaat tagccagcta gaatcttcct ggtcccttt tgaggcagta 4681 gcaggtaagg aaagggctga ttttcatcaa aaccaagacc tttctgcagg gatgatagtg 4741 gaataataat gtgggattag cccgctagca ttaggagcag ttgggaagtt acctggtaga 4801 tcaagcatta cacacaaaaa atcaagttga tcagagtatg ggttctccat atagcaatac 4061 ttcagtgaga ttaagtataa acagtttttg gcaaaaaaca acacagtcta ctctttctgc 4921 ttacaaagac aaagccttac aaactcacta tgaaggtaaa gggaggacag cttgcttctt 4981 tgcccagaca tttacaaagt tgtttttaaa acacactcat aagtaagttt ggcaagttgt 5041 ttaaaaaatg tctctttgtt ttgtacagtt ctgttagatg ttgttatatt ttaaaagttt 5101 aatttaaaaa atttaatttg tccttcctaa gaaggataaa tatataaaaa agccactgga 5161 atgaaaactt cctatatgct atgctgttgt cttattatta tatagaaaaa taactttaga 5221 aaaatattga agacattgta ttaccacttg tgattcaaac aattttgtgg ttaaaactgg 5281 attttaaatt taaaaatcaa taaaaatttc aaatgtt
```

The TERT gene, e.g., hTERT in humans, encodes a key enzymatic portion of telomerase protein complex in a cell. The hTERT promoter is turned on in telomerase-positive cancer cells, and is turned off in most normal somatic cells. HLTF binds to and regulates expression from the hTERT promoter and thus promotes MEC immortalization. DNA containing the sequence of this region of the hTERT promoter is used to inhibit binding of endogenous HLTF to the hTERT promoter for the purpose of inhibiting growth of tumors and progression of benign tumors to malignant tumors. In addition, antibodies, oligonucleotides, and HLTF-based peptides that inhibit binding of HLTF to the hTERT promoter are used for therapeutic and prophylactic interventions in individuals suffering from or at risk of developing malignant tumors. Since HLTF is a DNA binding helicase, inhibitors of these activities, i.e., DNA binding or helicase activity, inhibit HLTF activity and reduce hTERT transcription, thereby representing a treatment of cancer cells. SNF/SWI proteins such as HLTF participate in large protein complexes; therefore, inhibiting an HLTF interaction or binding with another member of the complex (e.g., a co-activator) also blocks its activity.

In addition to HPV-associated malignancies, e.g., cervical cancers, HLTF is overexpressed in other cancers (with no apparent HPV involvement), e.g., breast cancers. Methods of inhibiting HLTF expression or activity therefore confers clinical benefit to subjects suffering from HPV-associated as well as HPV-independent cancers.

Methods of Diagnosis

Diagnosis of a cancerous condition, e.g., a malignant tumor such as breast cancer, is based on detection of HLTF protein or mRNA. The method involves contacting a cell or a biological sample, e.g., a HPV-infected lesion from a subject with a compound that detects HLTF transcripts or gene products. The amount of transcript or gene product expressed in the cell or tissue sample is measured and compared to a control sample. An increase in HLTF indicates a malignancy or an increased risk of developing a malignancy.

The amount of HLTF in a cell, tissue (e.g., a tissue biopsy), or bodily fluid is measured by detecting gene transcripts (e.g., mRNA using northern blot assays or RT-PCR) or by detecting the gene product (e.g., by immunoblotting or immunohistochemistry). For example, a method for detecting the amount of HLTF protein or nucleic acid in a biological sample involves obtaining a biological sample from a test subject and contacting the biological sample with a compound or an agent capable of detecting HLTF protein or nucleic acid (e.g., mRNA, genomic DNA) that encodes HLTF protein. The agent is a labeled nucleic acid probe, which hybridizes to HLTF mRNA or DNA. The nucleic acid probe is a full-length HLTF nucleic acid, such as the nucleic acid of SEQ ID NO: , or a portion thereof, such as an oligonucleotide of at least 15, 30, 50, 100, 250 or 500 nucleotides in length and sufficient to specifically hybridize under stringent conditions to HLTF mRNA or DNA.

In addition to nucleic acid-based assays, an antibody that specifically binds to HLTF is used. The antibody is tagged with a detectable label. Antibodies are polyclonal, or more preferably, monoclonal. An intact antibody, or any antigen-binding fragment thereof (e.g., Fab or F(ab')$_2$) is used. Monoclonal antibodies, which specifically bind to HLTF were generated using standard methods. The antibody specifically detects HLTF in immunoblots and immunoprecipitation assays. The antibody binds to an epitope with HLTF amino acids 1-206 or 1-286 of SEQ ID NO: 10).

The term "labeled", with regard to the probe or antibody, encompasses direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The assays are carried out in vitro, ex vivo, or in vivo. In vivo techniques for detection of HLTF include introducing into a subject a labeled anti-HLTF antibody. For example, the antibody is labeled with a radioactive marker whose presence and location in a subject can be detected by standard imaging techniques. The amount of HLTF (gene product or gene transcript) is detected in the test sample and compared to an amount of HLTF gene product or transcript in a control sample.

In addition to solid tissue biopsies, bodily fluid such as blood, serum, and urine are tested. For example, the fluid is blood. HLTF protein is present in bodily fluids such as blood following necrosis of some cells of a tumor nodule and release of the protein (which is normally present in the nucleus or cytoplasm). This phenomenon occurs at the cancer progression stage at which the tumor is too large for its central core cells to get proper food and oxygenation. As the tumor grows, it recruits blood vessels (angiogenesis) to supply the large food and oxygen amounts needed for accelerated growth. At the time new blood vessels contact the necrotic cells, HLTF is release into the blood stream. HLTF in the blood and other bodily fluids is assayed using known methods, e.g., ELISA. In another example, HLTF is measured in urine for diagnosis of cancers such as prostate or bladder cancer.

The control sample is a value derived from a bodily tissue of an individual who is known not to have a cancer (e.g., a malignant tumor) based on earlier efforts to diagnose such pathologies. Alternatively, the control amount is an average of values from a plurality of non-cancerous individuals. To distinguish between benign and malignant tumors, the control amount is an amount derived from a benign tumor or a plurality of benign tumors.

Therapeutic Compositions and Methods

To prevent or treat a disease or condition associated with an HPV infection (e.g., a wart or an HPV-associated malignant tumor) or an aberrant HLTF expression or activity (e.g., breast cancer), a compound which modulates HLTF expression, is administered. A suspicious lesion or growth is contacted directly with the compound, e.g., by injecting the compound directly into the site of the lesion, or administered the compound systemically. To inhibit HLTF expression in a cell, the compound to be delivered to the cell is an HLTF-specific antisense nucleic acid or ribozyme.

Subjects to be treated are suffering from or at risk for a disease which is caused or contributed by aberrant HLTF expression or activity. Such individuals are identified by any or a combination of diagnostic or prognostic assays described herein. An HPV-infected individual (without an apparent tumor or HPV-associated lesion) is also at risk of developing an HPV-associated malignant tumor. HLTF-inhibitory agents are optionally administered prior to the manifestation of symptoms characteristic of the HLTF aberrancy to prevent progression to malignancy or after detection of malignancy to delay its progression.

Antisense therapy is used to inhibit expression of HLTF in patients, who are infected with HPV or who are suffering from or at risk of developing an HPV-associated malignant tumor. For example, an HLTF antisense oligonucleotide is directly introduced into the cells in a form that is capable of binding to the mRNA transcripts. Alternatively, a vector containing a sequence which, which once within the target cells, is transcribed into the appropriate antisense mRNA, is administered. Antisense nucleic acids, which hybridize to target mRNA, decrease or inhibit production of the polypeptide product encoded by a gene by associating with the normally single-stranded mRNA transcript, thereby interfering with translation and thus, expression of the protein. For example, DNA containing a promoter, e.g., a tissue-specific or tumor specific promoter, is operably linked to a DNA sequence (an antisense template), which is transcribed into an antisense RNA. By "operably linked" is meant that a coding sequence and a regulatory sequence(s) (i.e., a promoter) are connected in such a way as to permit gene expression when the appropriate molecules (e.g., transcriptional activator proteins) are bound to the regulatory sequence(s). Oligonucleotides complementary to various portions of HLTF mRNA are tested in vitro for their ability to decrease production of HLTF.

Small interfering RNAs (RNAi) are also used to decrease production of HLTF in cells. RNAi therapy is well suited to inhibit HLTF gene expression. RNAi incorporates expression of small interfering RNAs (siRNAs) in mammalian cells. These causes efficient and specific down-regulation of HLTF expression, causing stable functional inactivation of the target mRNAs (Zamore et al., 2002, Science 296: 1265–9; Brummelkamp et al, 2002, Science 296; 550–3).

Antisense therapy is carried out by administering to a patient an antisense nucleic acid by standard vectors and/or gene delivery systems. Suitable gene delivery systems include liposomes, receptor-mediated delivery systems, naked DNA, and viral vectors such as herpes viruses, retroviruses, adenoviruses and adeno-associated viruses, among others. A reduction in HLTF production results in a decrease in the progression of a tumor to malignancy. A therapeutic nucleic acid composition is formulated in a pharmaceutically acceptable carrier. Pharmaceutically acceptable carriers are biologically compatible vehicles which are suitable for administration to an animal: e.g., physiological saline. A therapeutically effective amount of a compound is an amount, which is capable of producing a medically desirable result such as reduced production of an HLTF gene product or a reduction in tumor growth in a treated animal.

HLTF-inhibitory compositions also include a dominant negative HLTF polypeptide or a nucleic acid aptamer. Such compositions inhibit HLTF dimerization or an interaction of endogenous HLTF with a co-activator protein leading to reduced HLTF activity in the cell.

Parenteral administration, such as intravenous, subcutaneous, intramuscular, and intraperitoneal delivery routes, are used to deliver nucleic acids or HLTF-inhibitory peptides or non-peptide compounds. Direct infusion into tumor site, e.g., a skin lesion, is carried out for local delivery of the therapeutic agent.

Dosages for any one patient depends upon many factors, including the patient's size, body surface area, age, the particular nucleic acid to be administered, sex, time and route of administration, general health, and other drugs being administered concurrently. Dosage for intravenous administration of nucleic acids is from approximately $10^2$ to $10^6$, more preferably $10^6$ to $10^{22}$, copies of the nucleic acid molecule.

The antisense nucleic acid molecules of the invention are typically administered to a subject or generated in situ such that they hybridize with or bind to cellular mRNA and/or genomic DNA encoding a protein to thereby inhibit expression of the protein, e.g., by inhibiting transcription and/or translation. In addition to local in situ delivery, an antisense nucleic acid molecule is modified to target selected cells and then administered systemically. For example, for systemic administration, an antisense molecule is modified such that it specifically binds to a receptor or an antigen expressed on a selected cell surface, e.g., by linking the antisense nucleic acid molecule to a peptide or an antibody which binds to a cell surface receptor or antigen (e.g., a receptor on the surface of an HPV-infected cell such as a human epidermal growth factor (EGF) or member of the human EGF receptor family). To achieve sufficient intracellular concentrations of the antisense molecules, vector constructs in which the antisense nucleic acid molecule is placed under the control of a strong promoter, such as a pol II or pol III promoter.

Ribozyme therapy is also be used to inhibit HLTF gene expression. Ribozymes bind to specific mRNA and then cut it at a predetermined cleavage point, thereby destroying the transcript. These RNA molecules are used to inhibit expression of the HLTF gene according to methods known in the art (Sullivan et al., 1994, J. Invest. Derm. 103:85S–89S; Czubayko et al., 1994, J. Biol. Chem. 269:21358–21363; Mahieu et al, 1994, Blood 84:3758–65; Kobayashi et al. 1994, Cancer Res. 54:1271–1275).

HLTF gene expression is inhibited by targeting coding sequences or nucleotide sequences, which are complementary to a regulatory region of the HLTF (e.g., the promoter and/or enhancer sequences) to form triple helical structures that prevent transcription of the HLTF gene in target cells.

In addition to inhibiting HLTF expression, compounds which inhibit binding of HLTF to a TERT promoter, e.g., hTERT promoter, are used to inhibit its activity. For example, the compounds are oligonucleotides, which bind to HLTF binding sites (bold type in FIG. 6 of the hTERT promoter region), thereby preventing endogenous HLTF from binding. In another example, the compounds are peptides, e.g., HLTF fragments, which bind to HLTF binding sites, but do not transactivate the promoter. Alternatively, the compounds are antibodies, which bind to HLTF. An endogenous HLTF molecule bound to an HLTF-specific antibody (the antibody or coding sequence of which is exogenously administerd) cannot bind to hTERT promoter sequences, and therefore, cannot transactivate the hTERT promoter.

Methods of Identifying Compounds that Inhibit HLTF Transactivation Activity

An assay to identify compounds that inhibit HLTF transactivation of the TERT promoter is carried out by comparing the level of TERT promoter activity in cells which the candidate compound is present compared to a parallel reaction in the absence of the compound (or a predetermined control value).

Candidate compounds, which inhibit HLTF transactivation of hTERT, are identified by detecting a reduction in transactivation in a cell which expresses or overexpresses HLTF, e.g., an HPV-infected cell. The HPV-infected cells are cultured in the presence of a candidate compound. Parallel cultures are incubated in the absence of the candidate compound. Transactivation is measured by methods known in the art, e.g., RPA or RT-PCR of the endogenous hTERT mRNA. A decrease in transactivation in the presence of the candidate compound compared to that in the absence of the compound indicates that the compound inhibits HLTF transactivation of the hTERT promoter and thereby inhibits carcinogenesis or progression of benign tumor cells to malignancy.

Candidate compounds that inhibit telomerase expression and cancer cell growth are identified using in vitro assays, which measure DNA binding and/or helicase activity using standard assays. For example, cells are incubated in the presence and absence of a candidate compound, and helicase activity measured using known methods, e.g., methods described by Hicham et al., 2000, Antiviral Res. 46:181–193 or Sivaraja et al, 1998, Anal. Biochem. 265:22–27. A decrease in helicase activity in the presence of a candidate compound (compared to the level of helicase activity in the absence of the compound) indicates that the compound inhibits HLTF activity. Similarly, HLTF binding to TERT promoter is measured in the presence or absence of a candidate inhibitor of DNA binding. Decrease HLTF/TERT promoter binding in the presence of the compound (compared to the level of binding in its absence) indicates that the candidate compound inhibits HLTF binding to promoter sequences and thereby inhibits transcription. Such assays are used to inhibit HLTF-mediated transcription. The assays are carried out using hTERT promoter sequences as well as other promoter sequences, e.g., SV40 promoter or plasminogen activator inhibitor-1 (PAI-1) promoter sequences. DNA binding or transcription from the test promoter is measured to determine whether a candidate compound inhibits DNA binding or transcription. An increase in DNA binding, helicase, activity, or transcription identifies a compound that is useful to prolong cell viability and immortality. For example, compounds that increase the binding of HLTF to the TERT promoter or increase HLTF helicase activity stimulate expression of hTERT and lead to immortalization. Methods of measuring HLTF-mediated transcription activity is carried out using methods known in the art, e.g., Ding et al., 1996, DNA Cell Biol. 15:429–442; Ding et al., 1999, J. Biol. Chem. 274:19573–19580). HLTF proteins and fragments are used to screen for inhibitors of telomerase activation and repression for use in controlling cell growth.

Production of HLTF-Specific Antibodies

Figure 5:
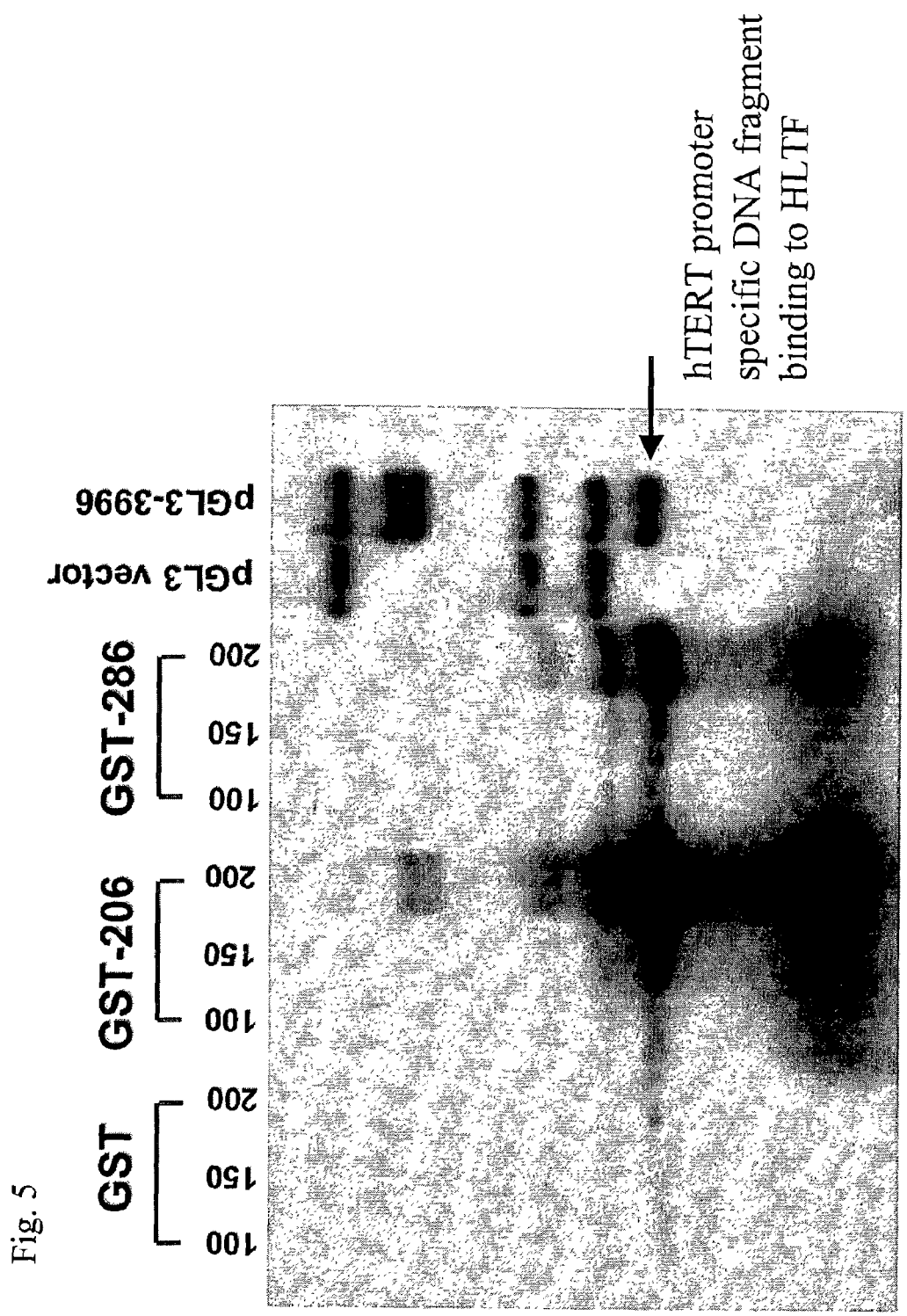
FIG. 5 is a photograph on an electrophoretic gel showing that HLTF binds to hTERT promoter DNA. Radiolabelled human telomerase reverse transcriptase (hTERT) promoter DNA was incubated with HLTF-GST fusion proteins, at salt concentrations of 100, 150 and 200 mM. After incubation, the fusion protein was selected using Glutathione Sepharose beads and washed several times to remove unbound DNA. DNA fragments that remained specifically bound to the HLTF-GST fusions were then eluted and analyzed by agarose gel electrophoresis. DNA fragments from pGL3 and pGL3-3996 which includes the hTERT promoter (last 2 lanes respectively) were incubated with GST, GST-206 or GST 286 (amino acids 1-206 and 1-286 of HLTF) and the unbound fragments washed off. 100, 150, and 200 are mM NaCl concentration in wash buffer.

Anti-HLTF antibodies are obtained by techniques well known in the art. Such antibodies are polyclonal or monoclonal. Polyclonal antibodies which bind to HLTF were obtained using standard methods, e.g., by the methods described in Ghose et al., Methods in Enzymology, Vol. 93, 326–327, 1983. An HLTF polypeptide, or an antigenic fragment thereof, was used as the immunogen to stimulate the production of polyclonal antibodies in the antisera of rabbits, goats, sheep, or rodents (e.g., using the method described in Ding et al., 1996, DNA Cell Biol. 15:429–442). Antigenic polypeptides for production of both polyclonal and monoclonal antibodies useful as immunogens include polypeptides which contain an hTERT promoter binding domain, i.e., amino acids 1-206 or amino acids 1-286 (as shown in Table 1 (SEQ ID NO: 10) and FIG. 5).

Antibody-producing hybridomas are made using standard methods. To identify those hybridomas producing antibodies that are highly specific for an HLTF polypeptide, hybridomas are screened using the same polypeptide immunogen used to immunize or a full-length HLTF protein. Antibodies which are identified as having HLTF-binding activity are also screened for the ability to inhibit HLTF transactivation activity. A preferred antibody has a binding affinity of at least about $10^8$ liters/mole and more preferably, an affinity of at least about $10^9$ liters/mole.

Monoclonal antibodies are humanized by methods known in the art, e.g, MAbs with a desired binding specificity can be commercially humanized (Scotgene, Scotland; Oxford Molecular, Palo Alto, Calif.; Dyax, Cambridge, Mass.).

HLTF-specific monoclonal antibodies are expressed in target cells intracellularly as follows. Following identification of a hybridoma producing a suitable monoclonal antibody, DNA encoding the antibody is cloned. DNA encoding a single chain HLTF-specific antibody in which heavy and light chain variable domains are separated by a flexible linker peptide is cloned into an expression vector using known methods (e.g., Marasco et al., 1993, Proc. Natl. Acad. Sci. USA 90:7889–7893 and Marasco et al., 1997, Gene Therapy 4:11–15). Such constructs are introduced into target cells, e.g., using standard gene delivery techniques for intracellular production of the antibodies. Intracellular antibodies are used to inhibit transactivation of hTERT promoter by endogenous cellular HLTF.

HLTF Cooperates with p53 Inactivation to Immortalize Human Cells

The E6 oncogene of the cancer-associated Human Papillomavirus (HPV) can induce cancers in mice, functionally inactivate p53 and immortalize human mammary epithelial cells (MEC). The ability of E6 to immortalize MEC may involve activation of telomerase as well as p53 inactivation. To identify additional E6 targets that contribute to cell immortalization and carcinogenesis, differential display was used to identify genes the expression of which is altered by E6. One example of an E6-induced gene is HLTF, which shares homology with the SWI/SNF family of transcriptional regulators. HLTF expression is low in normal MEC but is significantly increased in immortal MEC and breast cancer lines. Furthermore, p53 does not induce HLTF, but HLTF can bind to the hTERT promoter and stimulate hTERT expression. Introduction of HLTF into MEC together with dominant-negative p53 resulted in MEC immortalization. The data described herein indicate that HLTF and p53 represent two complementary targets of E6 that cooperate to induce MEC immortalization, and HLTF expression contributes to the development of mammary and HPV-associated carcinogenesis in vivo.

HPVs are DNA viruses that infect the proliferative layer of the epidermis and cause hyperproliferative lesions (warts), which occasionally progress to full malignancy. The high-risk HPV types are associated with cancers of the anogenital epithelium, e.g., cervical cancer. HPV oncogenic function has been mapped the early genes E6 and E7, which bind to and inactivate cellular tumor suppressor proteins p53 and Rb, respectively. While E6 and E7 cooperate to immortalize human foreskin keratinocytes (HFK), the high-risk E6 oncogene from HPV-16 can efficiently immortalize mammary epithelial cells (MEC), providing a useful culture system to assess E6-mediated transformation independently of E7. In this system, immortal cells acquire growth factor independence and thus can be selected by culture in the defined medium DFCI-2 (referred to as 'D2' medium), which lacks several growth factors normally required to support MECs growth in vitro.

Identification of an E6-Modulated Target Gene

The ability of E6 to immortalize MEC is believed to be linked to its abilities to inactivate p53 and to induce telomerase activation. However, additional targets may be involved, since E6 mutants that cannot induce p53 degradation retain immortalization capability. To identify such targets, gene expression profiles of normal MEC (strain 76N) and an isogenic E6-immortalized derivative (76-16E6) were compared using differential display (Liang et al., 1992, Science 257:967–971), a reverse transcriptase-polymerase chain reaction (RT-PCR) based transcriptional profiling method. A transcript was identified that was almost undetectable in normal 76N cells but is significantly increased in E6-immortalized cells, as well as in 76N cells transformed to full tumorogenicity by gamma radiation (FIG. 1). Increased expression of this transcript was also observed in MECs following immortalization by exposure to chemical agents. Sequence analysis of the cDNA revealed that it was identical to HLTF.

HLTF was identified as a factor that binds to various cellular and viral promoters, e.g., hTERT, SV40, and PAI-1. The cDNA shows homology to the SWI/SNF family of transcriptional regulators, which are thought to bind DNA and enhance the binding of transcriptional activators via displacement of nucleosomes along the DNA strand. In addition, HLTF possesses other functional domains, including a RING finger motif and a putative sequence-specific DNA binding domain, which are not generally shared by other SWI/SNF proteins.

To determine whether induction of HLTF expression is relevant to mammary carcinogenesis in vivo, HLTF expression was evaluated in primary MEC and a panel of breast cancer lines. As shown in FIGS. 2A–B, HLTF was highly expressed in all six cancer lines tested. These data indicate that induction of HLTF expression contributes to mammary carcinogenesis in vivo. HLTF induction was observed within a few days of introduction of E6, indicating that HLTF induction occurs early during immortalization and that HLTF is a transcriptional target of E6.

Increased HLTF expression could occur as a result of E6-dependent p53 inactivation, since p53 has been found to regulate transcription from multiple target promoters. HLTF expression levels were measured in primary MECs and MECs immortalized using E6 mutants that are unable to target p53 for degradation and the levels compared. These immortal lines retained high levels of functional p53. Elevated HLTF expression was found in these immortalized cells at levels comparable to that observed in cells immortalized using wild-type E6 (FIGS. 3A–B). These observations indicated that induction of HLTF expression does not occur as a result of p53 inactivation.

Figure 4A:
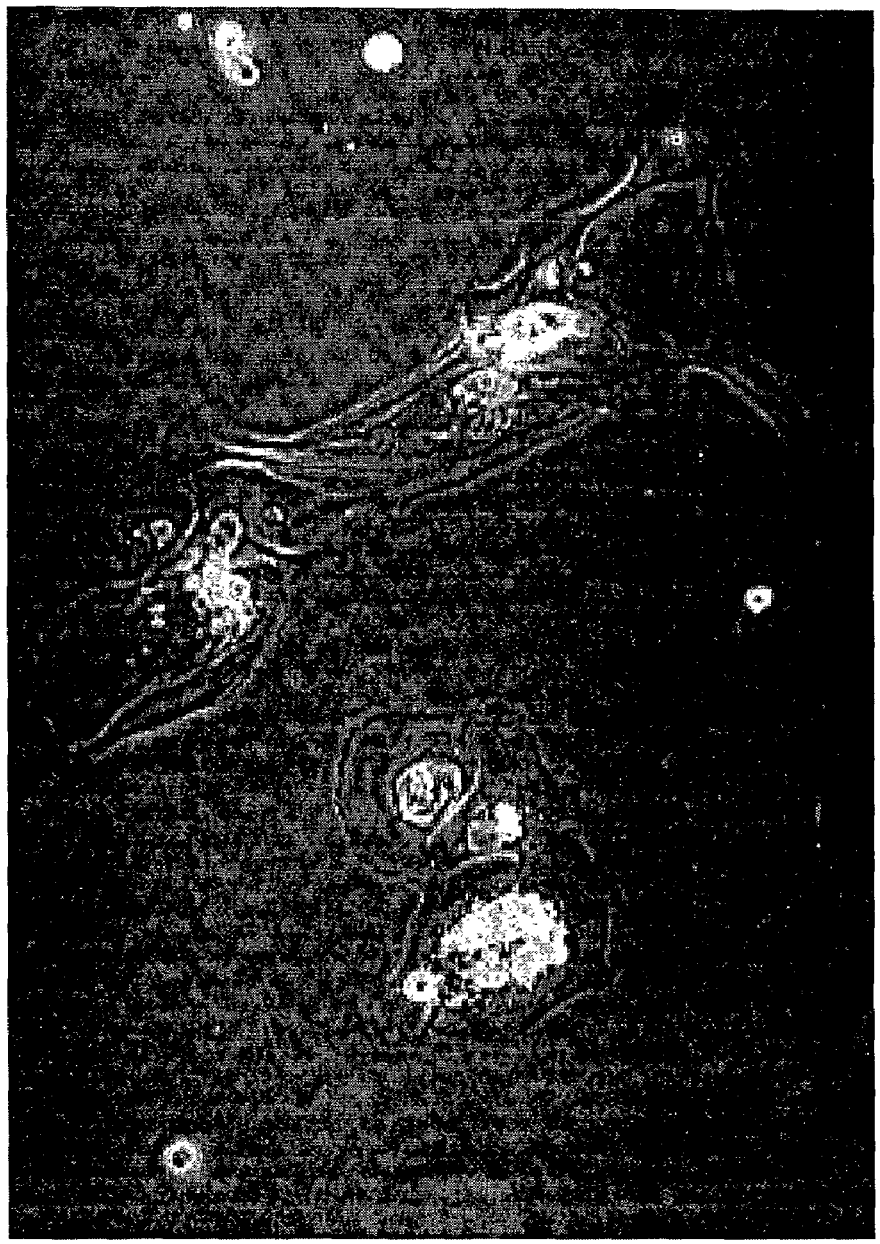
FIG. 4A shows GADPH, and FIG. 4B shows HLTF.
Figure 4B:
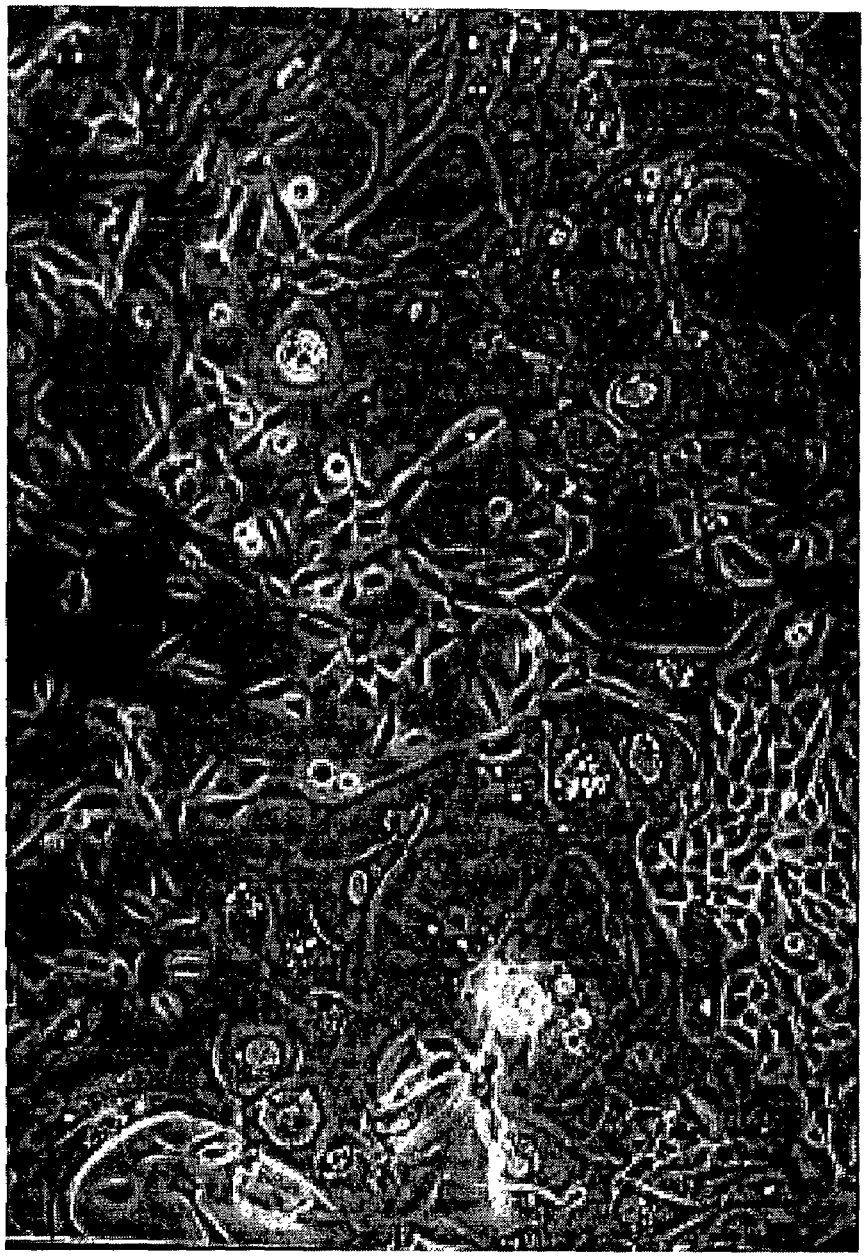

To define a biological role for HLTF in MEC immortalization, 76N cells were transfected with HLTF and passaged serially in D2 medium to select for cells that had acquired growth factor independence. An immortal population was not obtained following transfection of 76N cells with HLTF. However, E6 is a multifunctional protein that promotes growth via several pathways. Since the results indicated that HLTF induction and p53 inactivation represent distinct E6 activities, experiments were carried out to evaluate cooperation between HLTF expression and p53 inactivation during MEC immortalization. To induce p53 inactivation, a dominant-negative p53 mutant (dn-p53[R248W]) was used. The mutant can inhibit p53-mediated trans-activation in MEC but is unable to induce MEC immortalization. HLTF and dnp53[R248W] were co-transfected into MEC and the transfected population was serially passaged in D2 medium. While transfection with dn-p53 alone did not induce MEC immortalization, co-transfection with HLTF and dn-p53 followed by serial passage in D2 resulted in outgrowth of immortal cells (FIGS. 4A–B). This population displayed high levels of telomerase activity.

A mechanism by which HLTF contributes to immortalization was defined. HLTF binds to and activates promoters of cellular genes, e.g., hTERT, whose expression promotes MEC immortalization. To further study the mechanism, the N-terminus of HLTF, which possesses sequence-specific DNA binding activity, was fused to glutathione S-transferase (GST) and expressed in bacteria. This fusion protein was purified and incubated with radioactively labeled DNA derived from the 3996 most proximal nucleotides of the hTERT promoter region (positions −1 to −3996, FIGS. 5–6). In these experiments, specific and strong binding of HLTF to a 480 b.p. subregion of the hTERT promoter was observed (from position −3500 to −3996). These data indicate that full-length HLTF specifically binds this region of the hTERT promoter in vitro.

Addition of this "cold" competitor DNA containing this 480-nucleotide region inhibits binding of HLTF to the full-length promoter. In contrast, when a reduced region the HLTF N-terminus, containing amino acids 123–206, was purified and assayed for hTERT-DNA binding ability, no binding was observed. These data indicate that the HLTF small isoform, which lacks the N-terminal 123 residues, cannot bind DNA. HLTF-small thus represents an inactive form that antagonizes the function of full-length HLTF by competing with it.

Figure 7:
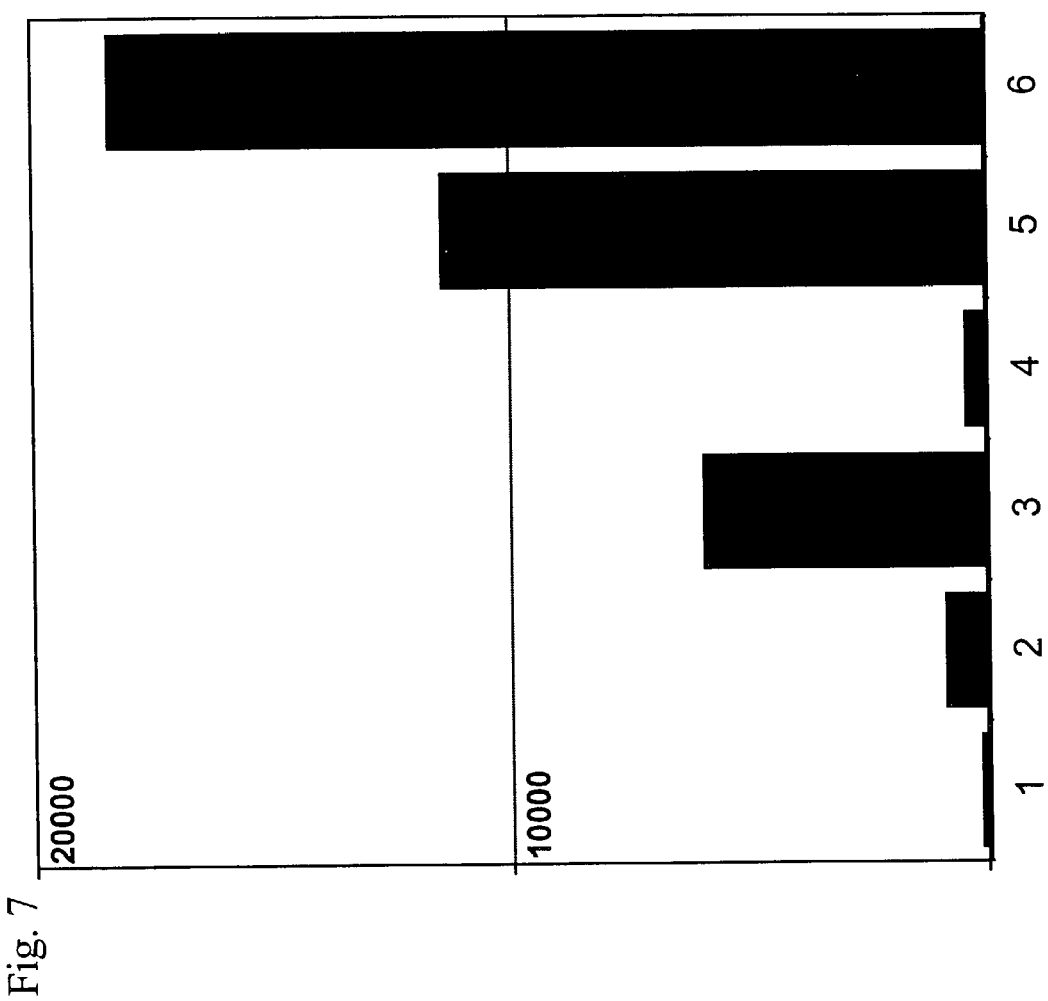
FIG. 7 is a bar graph showing that activation of the hTERT promoter regulates luciferase reporter gene expression. Data is expressed as luciferase activity. Each bar corresponds to a the following constructs: Lane 1: control; lane 2- vector alone; lane 3 HLTF; lane 4 HLTF deletion lacking amino terminal 122 amino acids; lane 5 HLTF; lane 6: HPV 16 E6.

The results also show that the ability of both HLTF isoforms to transactivate the hTERT promoter correlates with their ability to bind DNA. Each HLTP isoform was transfected into MEC together with a reporter construct (pGL3, from Promega) in which the luciferase gene was cloned downstream of the most proximal 3996 nts of the human hTERT promoter. The promoter region used contained the 480 nt region that HLTF binds. In these experiments, co-transfection with full-length HLTF enhanced the activity of the hTERT promoter from 5 to 7-fold, only a slight enhancement was observed when HLTF-small was used. The data indicated that full-length HLTF, but not HLTF-small, can activate the hTERT promoter in vivo (FIG. 7).

Other embodiments are within the following claims.

What is claimed is:

1. A method for diagnosing a breast neoplasm in a mammal, comprising measuring the level of helicase-like transcription factor (HLTF) in breast tissue of said mammal, wherein an increase in the level of HLTF in said tissue compared to the level in non-cancerous breast indicates the presence of a breast neoplasm in said tissue, wherein said measuring step comprises detecting a HLTF transcript in said tissue and wherein said transcript encodes the amino acid sequence of SEQ ID NO: 10.

2. A method for detecting the presence of a malignant breast tumor or a predisposition to developing said tumor, comprising contacting a sample of nucleic acid molecules obtained from a breast tissue biopsy with a nucleic acid probe which hybridizes under stringent conditions to a human HLTF nucleic acid transcript, wherein the transcript encodes the amino acid sequence of SEQ ID NO: 10, and determining the level of binding of said probe, wherein an increase in said binding compared to that in non-cancerous breast indicates the presence of a malignant breast tumor or a predisposition to developing said tumor, wherein said stringent conditions comprise a wash condition at 650° C. and a salt concentration of 0.1×SSC and wherein said probe comprises at least 15 nucleotides of SEQ ID NO: 9.

3. The method of claim 2, wherein said probe comprises at least 30 nucleotides of SEQ ID NO:9.

4. The method of claim 2, wherein said probe comprises at least 50 nucleotides of SEQ ID NO:9.

5. The method of claim 2, wherein said probe comprises at least 100 nucleotides of SEQ ID NO:9.

6. The method of claim 2, wherein said probe comprises at least 250 nucleotides of SEQ ID NO:9.

7. The method of claim 2, wherein said probe comprises at least 500 nucleotides of SEQ ID NO:9.

* * * * *

UNITED STATES PATENT AND TRADEMARK OFFICE
CERTIFICATE OF CORRECTION

| | |
|---|---|
| PATENT NO. | : 7,183,051 B2 |
| APPLICATION NO. | : 10/185369 |
| DATED | : February 27, 2007 |
| INVENTOR(S) | : Elliot J. Androphy et al. |

Page 1 of 1

It is certified that error appears in the above-identified patent and that said Letters Patent is hereby corrected as shown below:

Column 32, line 41, claim 2, "650° C." should read -- 65° C. --.

Signed and Sealed this

First Day of May, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,183,051 B2 | Page 1 of 1 |
| APPLICATION NO. | : 10/185369 | |
| DATED | : February 27, 2007 | |
| INVENTOR(S) | : Elliot J. Androphy et al. | |

It is certified that error appears in the above-identified patent and that said Letters Patent is hereby corrected as shown below:

Please insert the following paragraph at column 1, line 2, after the title:

--STATEMENT AS TO FEDERALLY SPONSORED RESEARCH

This invention was made with government support under CA073558 awarded by the National Institute of Health. The United States Government has certain rights in the invention.--

Signed and Sealed this

Fourth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,183,051 B2 Page 1 of 1
APPLICATION NO. : 10/185369
DATED : February 27, 2007
INVENTOR(S) : Elliot J. Androphy et al.

It is certified that error appears in the above-identified patent and that said Letters Patent is hereby corrected as shown below:

Please insert the following paragraph at column 1, line 2, after the title:

--STATEMENT AS TO FEDERALLY SPONSORED RESEARCH

This invention was made with government support under CA073558 awarded by the National Institute of Health. The United States Government has certain rights in the invention.--

Signed and Sealed this

Twenty-fifth Day of December, 2007

JON W. DUDAS
*Director of the United States Patent and Trademark Office*